United States Patent
Ochs-Onolemhemhen et al.

(10) Patent No.: US 8,404,457 B2
(45) Date of Patent: Mar. 26, 2013

(54) **ASSAY FOR DIAGNOSING *STREPTOCOCCUS PNEUMONIAE***

(75) Inventors: Martina Ochs-Onolemhemhen, Lyons (FR); Roger Brookes, Toronto (CA); Claire-Anne Siegrist, Geneva (CH)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 12/865,198

(22) PCT Filed: Feb. 2, 2009

(86) PCT No.: PCT/CA2009/000119
§ 371 (c)(1),
(2), (4) Date: Feb. 18, 2011

(87) PCT Pub. No.: WO2009/094779
PCT Pub. Date: Aug. 6, 2009

(65) Prior Publication Data
US 2011/0130300 A1    Jun. 2, 2011

Related U.S. Application Data

(60) Provisional application No. 61/063,376, filed on Feb. 1, 2008.

(51) Int. Cl.
*G01N 33/569* (2006.01)
*G01N 33/53* (2006.01)
(52) U.S. Cl. .................... 435/7.34; 435/7.2; 435/7.92
(58) Field of Classification Search .................... None
See application file for complete search history.

(56) References Cited

U.S. PATENT DOCUMENTS

| | | | |
|---|---|---|---|
| 6,716,432 B1 * | 4/2004 | Paton et al. ............ | 424/234.1 |
| 7,078,042 B2 | 7/2006 | Briles et al. | |
| 7,635,487 B2 * | 12/2009 | Meinke et al. ............ | 424/244.1 |
| 2003/0059438 A1 | 3/2003 | Briles et al. | |
| 2005/0048590 A1 | 3/2005 | Masure et al. | |
| 2006/0051361 A1 | 3/2006 | Laferriere et al. | |
| 2010/0227341 A1 | 9/2010 | Briles et al. | |

FOREIGN PATENT DOCUMENTS

| | | |
|---|---|---|
| CA | PCT/CA2009/000119 | 8/2009 |
| WO | 2004020609 A2 | 3/2004 |

OTHER PUBLICATIONS

Sanchez-Beato, et al. Molecular Characterization of PcpA: a novel choline-binding protein of *Streptococcus pneumoniae*. FEMS Microbiol. Lett. 164(1): 207-14 (1998).
GenBank Accession No. Q97NB5 (Oct. 31, 2006).
GenBank Accession No. Q04IN8 (May 26, 2012).
GenBank Accession No. P0C2J9 (May 16, 2012).
GenBank Accession No. Q7ZAK5 (May 16, 2012).
GenBank Accession No. ABO21381 (Jan. 11, 2010).
Hirst, et al. The role of pneumolysin in pneumococcal pneumonia and meningitis. Clin. Exp. Immunol. 138: 105-201 (2004).
GenBank Accession No. AAK06760 (Feb. 11, 2001).
GenBank Accession No. YP816370 (Jan. 25, 2012).
GenBank Accession No. NP358501 (Jan. 20, 2012).
GenBank Accession No. AAK06761 (Feb. 11, 2001).
GenBank Accession No. YP816371 (Jan. 25, 2012).
GenBank Accession No. NP358502 (Jan. 20, 2012).
GenBank Accession No. CAA09078 (Nov. 14, 2006).
GenBank Accession No. YP816335 (Jan. 25, 2012).
GenBank Accession No. ABJ55408 (Nov. 21, 2011).
GenBank Accession No. AAK19156 (Mar. 15, 2001).
GenBank Accession No. NP358461 (Jan. 20, 2012).
GenBank Accession No. AAK75086 (Nov. 21, 2011).
GenBank Accession No. CAB04758 (Nov. 14, 2006).
GenBank Accession No. YP817353 (Jan. 25, 2012).
GenBank Accession No. AAK76194 (Nov. 21, 2011).
GenBank Accession No. NP359536 (Jan. 20, 2012).
GenBank Accession No. ZP01835022 (Nov. 9, 2010).
GenBank Accession No. ZP01833419 (Nov. 9, 2010).

* cited by examiner

*Primary Examiner* — Padma V Baskar
(74) *Attorney, Agent, or Firm* — Patrick J. Halloran; Reza Yacoob

(57) ABSTRACT

Assays for detecting anti-streptococcal antibodies in biological samples using one or more streptococcal antigens are described herein. Various combinations of antigens may be used in the assays. For example, one or more of Ply, PhtD, PhtE, LytB and PcpA may be utilized. Additional streptococcal antigens may also be used. The assays may also be used in combination with assays that detect streptococcal nucleic acids.

12 Claims, 5 Drawing Sheets

ASSAY FOR DIAGNOSING *STREPTOCOCCUS PNEUMONIAE*

RELATED APPLICATIONS

This application was filed under 35 U.S.C. §371, and claims priority to International Application No. PCT/CA2009/000119, filed Feb. 2, 2009, which claims priority to U.S. Ser. No. 61/063,376 filed Feb. 1, 2008, each of which are incorporated herein by reference in their entirety.

FIELD OF THE DISCLOSURE

Described herein are reagents and methods for diagnosing bacterial infections.

BACKGROUND OF THE DISCLOSURE

Community-acquired pneumonia (CAP) is one of the most common pediatric infections, a major cause of morbidity in industrialized countries, and a leading cause of mortality worldwide in children under five years of age (Mulholland K, Lancet 2007; 370(9583): 285-9); Pio A, BWHO; 2003; 81(4): 298-300). CAP may be caused by multiple agents alone or in combination, including respiratory viruses, *Streptococcus pneumoniae, Haemophilus influenzae, Chlamydia* and *Mycoplasma pneumoniae* (Yin C C Respirology, 2003; 8(1):83-9; Chiang W C Respirology 2007; 12(2):254-61; Juven T PIDJ 2000; 19(4): 293-8). Etiological diagnosis is particularly challenging in young children, in whom blood cultures usually remain negative, bronchial secretions are rarely accessible, and frequent nasopharyngeal carriage limits the usefulness of microbial detection. Increasing the number of assays for pathogen detection nevertheless enhances the likelihood of the identification of a causal agent (Wang Pediatr Pulmonol 2008 feb 43(2)150-9; Nakayama E J Infect Chemother 2007, 13(5):305-13), and recent studies using modern diagnostic tools have repeatedly identified *S. pneumoniae* as a leading cause of CAP, both in primary-care, and in hospital settings (Juven T PIDJ 2000; 19(4): 293-8; Michelow I C; Pediatrics 2004; 113(4):701-7).

Protection against pneumococcal infection is essentially mediated by antibodies promoting opsonophagocytosis. Such antibodies may be directed against pneumococcal polysaccharides (PPS) or pneumococcal surface proteins (PSP). In the absence of pneumococcal immunization, such antibodies are elicited by pneumococcal exposure, colonization and/or infections. The lack of protective antibodies against pneumococcal antigens is thus at the basis of the vulnerability of infants and young children to pneumococcal disease. Although certain PSPs have been used in the serological diagnosis of pneumococcal infections, with excellent specificities and positive predictive values, such studies have frequently been limited by a low sensitivity in children. This was largely attributed to higher colonization prevalence interfering with serological analyses (Scott, et al. Clin. Diagn. Lab. Immunol. 2005).

The etiological diagnosis of pneumococcal pneumonia remains challenging, particularly in young children. Microbial diagnosis based on blood culture or DNA amplification has a high specificity but a low sensitivity in children who are rarely bacteremic. In contrast, high rates of nasopharyngeal colonization limits the sensitivity of assays detecting bacteria and/of fragments thereof in nasopharynx or urine samples (Dowell, S. F., *Clin. Infect. Dis.* 2000 32:824-825). The quest for a robust methodology of serological diagnosis of pneumococcal pneumonia has been met with many difficulties (Kanclerski, *J Clin Microbiol* 1988; Korppi M, *Eur J Clin Microbiol Infect Dis* 2007).

Diagnosis of community-acquired pneumonia (CAP) is particularly challenging in young children through traditional laboratory methods. There is a need in the field for reagents and methods useful for accurately and quickly diagnosing CAP, especially in young children. This need relates to both individual diagnosis, which requires assays providing rapid results with high sensitivities and negative predictive values to avoid useless antibiotic administration, and in epidemiological studies requiring assays with high specificity and positive predictive values for optimal case definition and adequate sensitivity to correctly estimate disease burden. Reagents and methods for accurately and quickly diagnosing CAP are described herein.

SUMMARY OF THE DISCLOSURE

Figure 1:
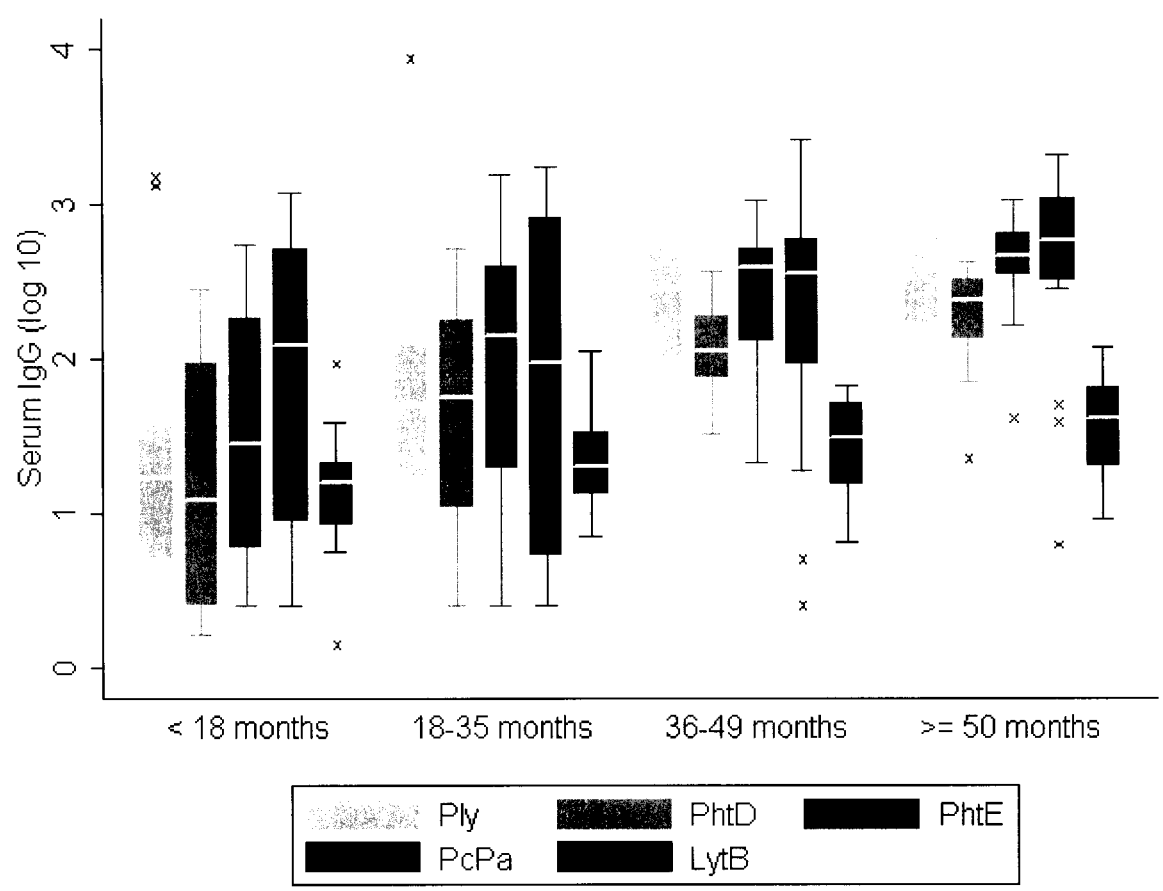
FIG. 1. Anti-PSP serum IgG antibodies at admission.

Assays for detecting anti-streptococcal antibodies in biological samples using one or more streptococcal antigens are described herein. Various antigens alone or combinations of antigens may be used in these assays. For instance, the assay may be performed to detect antibodies immunoreactive to Ply and one or more of PhtD, PhtE, LytB and PcpA; PhtD and one or more of Ply, PhtE, LytB and PcpA; PhtE and one or more of Ply, PhtD, LytB and PcpA; LytB and one or more of Ply, PhtD, PhtE, and PcpA; and/or PcpA and one or more of Ply, PhtD, PhtE, and LytB. The assays described herein may also be used with other streptococcal antigens in combination with one another and/or one or more of Ply, PhtD, PhtE, LytB, and/or PcpA. In this manner, sensitivity of the assay is increased and the negative predictive value is improved.

DETAILED DESCRIPTION

Provided herein are reagents and methods for accurately and quickly diagnosing community-acquired pneumonia (CAP) are described herein. The assays described herein overcome the low sensitivity of pneumococcal surface protein (PSP)-based immunoassays in children due to the traditional use of only one or a few immunogenic pneumococcal antigens. By detecting antibodies to a combination of bacterial antigens in the serum or other biological fluid of patient, a CAP diagnosis may be made. As shown herein, multiple PSPs were utilized as immunological probes to assess the pattern of humoral immunity driven by past exposure and acute pneumococcal infection in young children hospitalized for CAP. In one embodiment, the antigens may be selected from pneumolysin (Ply), PhtD, PhtE, LytB, and/or PcpA. The sequences of these five pneumococcal surface proteins are widely conserved across pneumococcal strains (>95-98%), allowing their use as markers of exposure to *S. pneumoniae* as well as vaccine candidates.

Pneumolysin (Ply) is a cytolytic-activating toxin implicated in multiple steps of pneumococcal pathogenesis, including the inhibition of ciliary beating and the disruption of tight junctions between epithelial cells (Hirst et al. Clinical and Experimental Immunology (2004)). Several pneumolysins are known and would be suitable in practicing the assays described herein including, for example GenBank Accession Nos. Q04IN8, P0C2J9, Q7ZAK5, and ABO21381, among others. In one embodiment, Ply has the amino acid sequence shown in SEQ ID NO.: 1.

PhtD polypeptides suitable for practicing the assays described herein include, for example, those of GenBank Accession Nos. AAK06760, YP816370 and NP358501, among others. In one embodiment, PhtD has the amino acid sequence shown in SEQ ID NO.: 2.

PhtE polypeptides suitable for practicing the assays described herein include, for example, those of GenBank Accession Nos. AAK06761, YP816371 and NP358502, among others. In one embodiment, PhtE has the amino acid sequence shown in SEQ ID NO.: 3.

LytB polypeptides suitable for practicing the assays described herein include, for example, those of GenBank Accession Nos. CAA09078, YP816335, ABJ55408, AAK19156, NP358461, and AAK75086, among others. In one embodiment, LytB has the amino acid sequence shown in SEQ ID NOS.: 4, 5 or 8.

PcpA was first cloned and characterized in 1998 as a choline-binding protein with a putative adhesion role (Sanchez-Beato *A FEMS Microbiology Letters* 164 (1998) 207-214). PcpA polypeptides suitable for practicing the assays described herein include, for example, those of GenBank Accession Nos. CAB04758, YP817353, AAK76194, NP359536, ZP01835022, and ZP01833419, among others. In one embodiment, PcpA has the amino acid sequence shown in SEQ ID NOS.: 6 or 7.

The antigens may be used in the assays described herein, either alone or in combination with one another. The use of single antigens or any combination of antigens may be suitable for use in the assays described herein provided the assay demonstrates the desired sensitivity and negative predictive values. In certain embodiments, the use of a combination of antigens may result in a sensitivity of approximately, 0.80, 0.85, 0.90, 0.91, 0.92, 0.93, 0.94, 0.95, 0.96, 0.97, 0.98, 0.99, or 1.0 with a negative predictive value of approximately 0.80, 0.85, 0.90, 0.91, 0.92, 0.93, 0.94, 0.95, 0.96, 0.97, 0.98, 0.99, or 1.0. In some embodiments, the values are significant. Comparisons may be performed and significance determined using any of the available statistical analysis tools, alone or in combination with one another, including, for example, student's T-test, chi-square test, Fisher's exact test, analysis of variance (ANOVA), univariate statistical analyses, logistic regression analysis to calculate adjusted odds ratio (OR) and 95% confidence interval (CI). Conrols for any statistically significant demographic variables that might function as confounders (gender, etc) may also be utilized. Differences between values are typically considered significant at $p<0.05$ or $p<0.01$, for example. Other statistical analysis tools may also be used.

For instance, the assays may be performed to detect antibodies immunoreactive to only one of Ply, PhtD, PhtE, LytB or PcpA, without assaying for antibodies reactive to any other antigen. Alternatively, the assay may be performed to detect antibodies immunoreactive to more than one of Ply, PhtD, PhtE, LytB and/or PcpA. For instance, the assay may be performed to detect antibodies immunoreactive to Ply and one or more of PhtD, PhtE, LytB and PcpA; PhtD and one or more of Ply, PhtE, LytB and PcpA; PhtE and one or more of Ply, PhtD, LytB and PcpA; LytB and one or more of Ply, PhtD, PhtE, and PcpA; and/or PcpA and one or more of Ply, PhtD, PhtE, and LytB. The assay may also be performed to identify antibodies immunoreactive to combinations of antigens such as PcpA and Ply; PcpA and PhtD; PcpA and PhtE; PcpA and LytB; PcpA, Ply, and PhtD; PcpA, Ply, PhtD, and PhtE; Ply, PhtD, PhtE, and LytB; PcpA, PhtD, and PhtE; PcpA, PhtD, PhtE, and LytB; PcpA, PhtE, and LytB; PcpA, Ply, PhtE, and LytB; PcpA, PhtD, and LytB; PcpA, Ply, and LytB; PcpA, Ply, PhtD, and LytB; PcpA, Ply, and PhtE; and/or, PcpA, PhtD, and PhtE. Other combinations will be apparent to one of skill in the art given this disclosure. The assays described herein may also be used with other streptococcal antigens in combination with one another and/or one or more of Ply, PhtD, PhtE, LytB, and/or PcpA.

In certain embodiments, an isolated and purified PcpA protein or immunologically reactive fragment thereof may be used for detecting a past infection or active infection by *Streptococcus pneumoniae* in a subject by detecting the binding of antibodies in a sample obtained from a subject to said isolated and purified PcpA antigen (e.g., protein or immunologically reactive fragment thereof). In other embodiments, the isolated and purified PcpA antigen may be used with at least one additional antigen (e.g, PhtD, PhtE, LytB and/or Ply protein or immunologically reactive fragment thereof). Thus, a method of detect the presence of and/or diagnosing *pneumoniae* or infection by *S. pneumoniae* in a subject comprising detecting in a biological sample from said subject antibodies against one or more PcpA, PhtD, PhtE, LytB, and/or Ply antigens, wherein the presence of antibodies that bind to the antigen(s) is indicative of infection, is provided. In certain embodiments, the method comprises contacting a biological sample derived from a subject with the isolated or purified PcpA, PhtD, PhtE, LytB, and/or Ply antigens of *S. pneumoniae* for a time and under conditions sufficient for an antigen-antibody complex to form and then detecting the formation of an antigen-antibody complex. Detection of the antigen-antibody complex may be achieved by detecting human immunoglobulin in the complex. In certain embodiments, detection of the antibody may be accomplished by contacting the antigen-antibody complex with a "second" antibody that is immunologically reactive with human immunoglobulin (e.g., anti-human immunoglobulin antibody) for a time and under conditions sufficient for the second antibody to bind to the human immunoglobulin in the complex and then detecting the bound anti-human immunoglobulin. It is preferred that the second antibody is labelled with a detectable marker or reporter molecule.

A method is also provided for determining the response of a subject having pneumonia or an infection by *Streptococcus pneumoniae* to treatment with a therapeutic compound. The method involves detecting antibodies against a PcpA antigen in a biological sample of the subject after treatment, wherein the amount of antibody detected is increased, unchanged, or decreased as compared to the amount of antibody detectable in a biological sample of the subject obtained prior to treatment, or to that of a normal or healthy subject. In one embodiment, an unchanged or decreased amount of antibody after treatment may indicate that the subject is not responding to treatment. In another embodiment, an unchanged or decreased amount of antibody after treatment may indicate that the subject is responding to treatment. In another embodiment, an increased amount of antibody after treatment may indicate that the subject is not responding to treatment. In another embodiment, an increased amount of antibody after treatment may indicate that the subject is responding to treatment. Treatment regimens may then be adjusted accordingly.

The antigens may be used in these assays as full-length polypeptides. However, the antigens may be related antigens such as, for example, fragments, variants (e.g., allelic, splice variants), orthologs, homologues, and derivatives (e.g., peptides, fusions) that retain reactivity to antibodies found in the biological sample. A fragment, variant, or derivative may have one or more sequence substitutions, deletions, and/or additions as compared to the subject sequence. Fragments or variants may be naturally occurring or artificially constructed. In one embodiment, such related antigens may be prepared from the corresponding nucleic acid molecules. In preferred embodiments, the related antigens may have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions. Related antigens may include peptides, which are typically a series of contiguous amino acid residues having a sequence corresponding to at least a portion of the polypeptide from which it was derived. In preferred embodiments, a peptide may include about 5-10, 10-15, 15-20, 30-20, or 30-50 amino acids.

Substitutions may be conservative, or non-conservative, or any combination thereof. Conservative amino acid modifications to the sequence of an antigen (and/or the corresponding modifications to the encoding nucleotides) may produce a related antigen having functional and chemical characteristics similar to those of parental antigen. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particular, does not result altered function of the antigen (e.g., does not cause decreased immunogenicity or reactivity with antibodies in the biological sample). Suitable, exemplary conservative amino acid substitutions are shown below:

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Fragments may include antigens with particular regions or domains deleted. It may be beneficial to delete such regions or domains where, for instance, the presence of those regions or domains will interfere with the use of the fragments in the assays described herein. For instance, when using PcpA, Ply, PhtD, PhtE or LytB, the cholinergic binding region may be deleted. An exemplary fragment of PcpA protein is shown in SEQ ID NO.: 7.

In other embodiments, the antigen may include one or more fusion polypeptide segments that assist in purification and/or detection of the antigen. Fusions can be made either at the amino terminus or at the carboxy terminus of the antigen. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fused moieties may be derivatized or otherwise manipulated, as is known in the art or according to the methods described herein. Suitable fusion segments include, among others, metal binding domains (e.g., a poly-histidine segment), immunoglobulin binding domains (e.g., Protein A, Protein G, T cell, B cell, Fc receptor, or complement protein antibody-binding domains), sugar binding domains (e.g., a maltose binding domain), and/or a "tag" domains (e.g., at least a portion of α-galactosidase, a strep tag peptide, a T7 tag peptide, a FLAG peptide, or other domains that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage.

In certain embodiments, the antigen may be directly or indirectly (e.g., using an antibody) labeled or tagged in a manner which enables it to be detected. An antigen may be directly labeled by attaching the label to the antigen per se. An antigen may be indirectly labeled by attaching a label to a reagent that binds to the antigen, such as an antibody or other moiety. Suitable labels include, for example, fluorochromes such as fluorescein, rhodamine, phycoerythrin, Europium and Texas Red; chromogenic dyes such as diaminobenzidine, radioisotopes; macromolecular colloidal particles or particulate material such as latex beads that are coloured, magnetic or paramagnetic; binding agents such as biotin and digoxigenin; and, biologically or chemically active agents that can directly or indirectly cause detectable signals to be visually observed, electronically detected or otherwise recorded, for example in a FACS, ELISA, western blot, TRFIA, immunohistochemistry, evanescence, Luminex bead array, dipstick, or other lateral flow assay format. Suitable antibody-binding molecules for use in such methods may include immunoglobulin-binding antibodies, for example anti-human antibodies (e.g., anti-human antibodies specific for Ig isotypes or subclasses (e.g., of IgG), or specific for Staphylococcal protein A or G.

Preferred fluorescent tag proteins include those derived from the jelly fish protein known as green fluorescent protein (GFP). Further information on GFP and other fluorophores is given in the following publications: Tsien R Y, "The Green Fluorescent Protein" Annual Reviews of Biochemistry 1998; 67:509-544 Verkhusha, V. and Lukyanov, K. "The Molecular Properties and Applications of Anthoza Fluorescent Proteins and Chromophores" Nature Biotechnology 2004; 22:289-296. Plasmid vectors encoding a wide range of fluorescent tag proteins are commercially available from various suppliers including an array of "Living Colours 8482; Fluorescent Proteins" available commercially from Clontech Laboratories, Inc. Similar vectors can also be obtained from other suppliers including Invitrogen and Amersham Biosciences. Suitable fluorescent proteins derived from GFP are the red-shifted variant EGFP, the cyan shifted variant ECFP and the yellow shifted variant EYFP. EGFP is preferred as the fluorescent marker because it gives bright fluorescence combined with minimal effect on the antigenic properties of the target antigen. Alternative fluorescent marker proteins are commercially available. Biologically or chemically active agents include enzymes, which catalyse reactions that develop or change colours or cause changes in electrical properties, for example, and may also be utilized. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples include horseradish peroxidase and chemiluminescent reagents. In some embodiments, the non-immobilized antibody-binding molecule or polypeptide may be detected using an antibody which binds to said non-immobilized antibody-binding molecule or polypeptide. A suitable detection antibody may be labeled by means of fluorescence. In some embodiments, the label may be a fluorescent marker (tag) which is used to label the target antigen directly such that the antigen and the fluorescent marker form a fusion protein.

If antibodies against the target antigen are present in a biological sample, the antigen or antibody may be labeled with a tag, and the antigen-antibody complex formed may be detected by, for example, immunoprecipitation. The fluorescence associated with the tag may then be used to determine that protein has been precipitated (qualitative determination) or to determine the amount of protein precipitated (quantitative determination). For example, soluble extracts of a fluorescence-tagged antigen may be incubated with patient sera for an appropriate period of time such as overnight at 4° C. (typically 10-15 µl of serum to 300-500 µl of extract or less) to allow antibodies to bind to the antigen. Protein A or Protein G Sepharose beads, preincubated with low IgG fetal calf serum (Sigma) to block non-specific binding, are then added to the extract/serum mix containing the tagged antigen/antibody complexes, and mixed with gentle rotation for 1 to 2 hours at room temperature. The antibodies within the serum, including those that specifically bind the tagged antigen, are bound by the protein A/G beads. The protein A/G Sepharose beads are then washed in a suitable buffer (typically 10 mM Tris-HCl pH 7.4, 100 mM NaCl/ImM EDTA/1% Triton X-100) to remove any unbound tagged antigen. This may be achieved by multiple (e.g., 2, 3, 4, or 5) rounds of centrifugation, removal of the supernatant, and resuspension in buffer. The beads, some with tagged antigen attached, are then collected and placed in a fluorescence reader, for example a Spectra Max Gemini XS plate reader from Molecular Devices, Inc. The presence of antibodies in the sample may then be quantitated. In the case of GFP, detection may be accomplished using excitation at wavelength 472 nm and emission at 512 nm. The fluorescence excitation will depend upon the fluorophore/tag that is used but it would be possible to combine several different tagged proteins in the same time. For example, one or more of Ply, PhtD, PhtE, LytB and/or PcpA may be separately tagged and separately or simultaneously assayed. The sensitivity of the method is dependent on the detection device and can be considerably enhanced by using more sensitive detection devices. Various modifications of these methods could also be utilized. Other labels are available in the art and may be suitable for use the assays described herein.

The assays described herein for detecting antibodies immunoreactive with streptococcal antigens may also be combined with other assays useful for detecting streptococcal infection. For instance, these assays (i.e., ELISA) may be combined with polymerase chain reaction (PCR) assays for detecting streptococcal nucleic acid in a biological sample. Alternatively, an ELISA assay may be combined with an immunoprecipitation assay. Or, a PCR-based assay may be combined with an immunoprecipitation assay. Combining the various assays described herein may serve to even further increase the sensitivity of detection and further decrease the negative predictive value of the data.

Also provided herein as kits for detecting the presence of streptococcus infection in a patient by detecting antibodies or nucleic acid in a biological sample of the patient. In one embodiment, one or more pneumococcal antigens (i.e., Ply, PhtD, PhtE, LytB, and/or PcpA) may form part of a kit for detecting or diagnosing anti-streptococcal antibodies in a biological sample. The antigens may be provided in a suitable container such as a vial in which the contents are protected from the external environment. Thus, a kit for detecting an anti-streptococcal antibody in a sample may comprise an antigen (i.e., Ply, PhtD, PhtE, LytB, and/or PcpA) along with one or more detection reagents for determining binding of one or more antibodies in a sample to the antigen is provided. The kit preferably includes: (i) one or more isolated and purified PcpA, PhtD, PhtE, LytB and/or PcpA proteins or immunologically reactive fragments thereof of *S. pneumoniae*; and (ii) means for detecting the formation of an antigen-antibody complex, optionally packaged with instructions for use.

The antigen(s) may be free in solution or may be immobilized on a solid support, such as a magnetic bead, tube, microplate well, or chip. In certain embodiments, a solid matrix comprising an isolated and purified PcpA, PhtD, PhtE, LytB, and/or PcpA protein or immunologically reactive fragment thereof or a fusion protein or protein aggregate adsorbed thereto is provided. In some embodiments, the kit may further comprise an antibody-binding molecule as a detection reagent. The antibody-binding molecule may be a capture or detection reagent and may be free in solution or may be immobilized on a solid support, such as a magnetic bead, tube, microplate well, or chip. The antibody-binding molecule or polypeptide may be labeled with a detectable label, for example a fluorescent or chromogenic label or a binding moiety such as biotin. Suitable labels are described in more detail above. The kit may further comprise detection reagents such as a substrate, for example a chromogenic, fluorescent or chemiluminescent substrate, which reacts with the label, or with molecules, such as enzyme conjugates, which bind to the label, to produce a signal, and/or reagents for immunoprecipitation (i.e., protein A or protein G reagents). The detection reagents may further comprise buffer solutions, wash solutions, and other useful reagents. The kit may also comprise one or both of an apparatus for handling and/or storing the sample obtained from the individual and an apparatus for obtaining the sample from the individual (i.e., a needle, lancet, and collection tube or vessel). The kit may also include instructions for use of the antigen, e.g. in a method of detecting anti-streptococcal antibodies in a test sample, as described herein. Where the assay is to be combined with another type of assay such as PCR, the required reagents for such an assay (i.e., primers, buffers and the like) along with, optionally, instructions for the use thereof, may also be included.

A better understanding of the present invention and of its many advantages will be had from the following examples, given by way of illustration.

EXAMPLES

Example 1

Materials and Methods

Ninety-nine children aged 2 months to 6 years were enrolled in a prospective cohort study at admission for CAP to the pediatric wards of the University Hospitals of Lausanne and Geneva (Switzerland) between March 2003 and December 2005. Children were eligible if presenting with clinical signs of pneumonia according to the WHO classification (ref), children with actively treated asthma, chronic illness or underlying disease, immunosuppression or presenting with wheezing (suspected bronchiolitis) being excluded. None had been immunized against *S. pneumoniae*, according to the Swiss recommendation in 2003-2005. They were enrolled after signed parental content, as approved by the Ethical Committee of both institutions.

Blood, urine and nasopharyngeal samples were cultivated within 8 hours of admission and assessed for the presence of viruses or bacteria. PCR analyses on nasopharyngeal samples included 13 viruses, *Mycoplasma pneumoniae*, and *Chlamydia pneumoniae*, whereas blood samples were assessed by Ply-specific PCR. All chest radiographs taken at admission were reviewed by a senior radiologist blinded to clinical and laboratory findings. Convalescent serum samples were obtained 3 weeks later for 75/99 children who had not been previously immunized against *S. pneumoniae*. These 75 children were included in this study on CAP-associated anti-pneumococcal responses.

The PhtD, PhtE, PcpA and LytB proteins used in this study are recombinant proteins expressed in *E. coli*. The PhtD and PhtE used are full-length proteins and the PcpA and LytB used are truncated forms with the choline-binding domain removed. All four proteins are expressed in *E. coli* as soluble proteins and purified with combinations of ion exchange chromatography. All protein has $\geq$90% purity after purification as assayed by SDS-PAGE and RP-HPLC.

Paired acute and convalescent serum samples were stored at $-20°$ C. until analysis. Samples were encoded prior to transfer to the laboratory and IgG antibodies to Ply, PhtD, PhtE, PcpA and LytB were measured blindly by laboratory personal unaware of clinical data. Paired serum samples were tested in the same run by indirect ELISA using purified proteins to coat Immulon (Thermo Labsystem) plates. Eight serial dilutions of each serum sample were performed to allow quantification of antibody titers. After 60 min at 37° C., anti-IgG antibody conjugated to horseradish peroxydase (Cappel) was added, followed by ABTS as the substrate. The ELISA titer of each serum was defined by comparison to a reference human AB serum, used in each assay, to which ELISA Units were arbitrarily assigned by taking the reciprocal of its dilution at OD=1.0. Results were expressed in EU/ml. Serum with titers below the assay cut-off of 5 EU/ml were given a titer of 2.5 EU/ml. Antibody titers were log transformed to allow comparisons of mean geometric concentrations (GMC). A significant rise in antibody titers was predefined as a minimal two-fold (100%) increase between the acute- and convalescent-phase samples.

Socio-demographic characteristics of the participants are described using standard descriptive statistics (frequencies, means, geometric means, and standard deviation). Comparison of different serologies were performed using Student's T-test, while categorical data were compared using chi-square tests or Fisher's exact test when appropriate. Serologies among groups were compared by using analysis of variance (ANOVA). Univariate statistical analyses were performed for each variable to determine its relationship to the dependent variable, being a case patient or not. Logistic regression analysis was used to calculate adjusted odds ratio (OR) and 95% confidence interval (CI), controlling for any statistically significant demographic variables that might function as confounders (gender, etc). For all statistical tests, differences were considered significant at p<0.05 or when the 95% CI did not include 1.0. SPSS (version 15.0) statistical-software program was used for analyses.

Example 2

Experimental Results

A. Evidence of Acute Pneumococcal Infection in Children with Cap

Seventy-five previously healthy children (mean age 33.7 months, median 35.4 months, range 2.6 to 66 months, 50% females) were enrolled at admission and provided both acute and convalescent sera for this prospective study of CAP-associated anti-pneumococcal immunity. Only one child had a positive blood culture whereas 15/75 (20%) patients had pneumolysin DNA (Ply$^+$-PCR) in their blood. The use of serum IgG seroresponses to Ply ($\geq$2-fold increase between acute and convalescent sera) identified 16/75 (21%) children with evidence of an acute pneumococcal infection (Table 1). This proportion increased to 31% (23/75) when combining Ply$^+$-PCR and/or anti-Ply seroresponses, which is in accordance with recent reports (reviewed by Korppi M, *Eur J Clin Microbiol Infect Dis* 2007).

To identify further children with evidence of acute pneumococcal infection, we used four additional PSP (PhtD, PhtE, LytB, and PcpA) as immunological probes to quantify antibody titers in the 75 paired acute and convalescent serum samples. Responses to LytB were rare (Table 1). In contrast, significant ($\geq$2-fold) IgG responses were observed in 21-32% of children hospitalized with CAP (Table 1). Altogether, 34/75 (45%) children had evidence of an acute response to *S. pneumoniae*. The mean fold-changes in serum IgG antibodies were marked for anti-PhtD (4.22), anti-PhtE (6.88) and anti-PcpA (5.62), moderate for anti-Ply (2.15) and weak for anti-LytB (1.51). Age did not influence the fold change of serum anti-PSP antibodies ($R^2$<0.162 for each PSP), indicating that even young infants may raise anti-PSP responses to acute pneumococcal infection. This was confirmed by the observation of three 8-10 months old infants with marked seroresponses (mean 2.88-6.82 fold changes) to PhtD, PhtE, and PcpA. Last, seroresponses were frequently directed against several PSP ($\geq$2 PSP: 30%, $\geq$3 PSP: 25%, $\geq$4 PSP: 14%, $\geq$5 PSP: 1%), providing strong evidence of recent pneumococcal exposure.

The 34/75 (45%) children with acute seroresponses to $\geq$1 PSP included 86% (13/15) Ply$^+$-PCR patients. Only 2 Ply$^+$-PCR children lacked anti-PSP response: a 2.6-month-old boy, presumably too young to rapidly raise infection-driven B cell responses, and a 43-month-old girl admitted with a 17-days history of cough, and 7 days of fever, who already had high acute serum titers against the 5 PSP when eventually admitted with lobar pneumonia. Thus, combining Ply$^+$-PCR and seroresponses to a panel of 5 PSP identified 36/75 (48%) children hospitalized for CAP as with strong evidence of acute pneumococcal infection (P-CAP).

B. Immunoprobes for the Diagnosis of Pneumococcal CAP in Young Children

The 36 CAP children with evidence of acute pneumococcal responses ($\geq$2-fold rise) and/or infection (Ply$^+$-PCR) (P-CAP) to 31 children with no evidence of recent pneumococcal exposure (negative Ply PCR and lack of a $\geq$2-fold rise of IgG titer to any PSP (NP-CAP) were studied. Eight children with very high (>300 EU/ml) admission serum titers against $\geq$3 PSP were excluded from these analyses to avoid attribution errors, as high anti-PSP may reflect recent exposure or infection while limiting the likelihood of a $\geq$2-fold response. Such an approach sets the assay's specificity and positive predictive value at 1.00, as responders are by definition not included in the control group. However, it allows comparing assay sensitivity and negative predictive values in well-controlled study groups. Relying on Ply$^+$-PCR alone to diagnose pneumococcal CAP would have missed $^{19}/_{36}$ (53%) patients, in accordance with the fact that pneumococcal pneumonia is seldom bacteremic. The use of anti-Ply IgG responses alone would have missed $^{17}/_{36}$ (47%) children, yielding a sensitivity of 0.44 and a negative predictive value of 0.61 that are also in accordance with previous reports (Table 1). Higher values resulted from the use of either anti-PhtE or anti-PcpA alone (Table 1). As postulated, combining several PSPs further increased assay sensitivity (Table 2). The combination of anti-PcpA and anti-PhtE responses resulted in a sensitivity of 0.92, with a negative predictive value of 0.91. These values were further increased by adding anti-Ply responses, the combination of anti-PcpA, PhtE and Ply responses yielding the optimal result of 0.94 for both sensitivity and negative predictive values. Importantly, the maximal sensitivity of any combination of PSP that does not include PcpA remained below 0.68. This confirms that increasing the number of antigens enhances the likelihood of the identification of a causal agent of CAP, and that certain immunoprobes more significantly contribute to the diagnosis of pediatric pneumococcal CAP than others.

C. Clinical Characteristics of Children with Pneumococcal or Non-Pneumococcal CAP It was then of interest to determine whether children with strong evidence of acute pneumococcal infection (P-CAP, n=36) differed in their demographic or clinical characteristics from children (n=31, NP-CAP) without evidence of recent pneumococcal exposure. Univariate analyses indicated that neither age (33.5 vs 32.7 months), gender (50% vs 48% females), clinical severity of pneumonia (WHO score I: 5 vs 1, II: 23 vs 21, III: 7 vs 9), duration of cough (7 vs 4 days), duration of fever (4.2 vs 3.2 days) nor antibiotic use within 30 days of admission (9 vs 8 children) differed in children hospitalized for P-CAP or NP-CAP. This confirms that clinical patterns alone may not reliably identify children with CAP of pneumococcal origin.

D. Distinct Pneumococcal Immunity in Children Admitted for Pneumococcal or Non-Pneumococcal CAP Given the importance of preexisting anti-pneumococcal antibodies in protection against *S. pneumoniae* infection, we used a common reference serum to compare PSP-specific immunity at admission and possibly identify differences among P-CAP and NP-CAP children. All 75 patients had detectable serum antibodies to at least one protein and most to several PSP ($\geq$2 PSP: 96%, $\geq$3 PSP: 92%, $\geq$4 PSP: 89%, $\geq$5 PSP: 86%). The highest GMTs were directed against PcpA, Ply and PhtE, while anti-LytB antibodies were significantly lower (Table 3). Antibody titers at admission were markedly heterogeneous. As both pneumococcal exposure and B cell response capacity increase with age, we searched for correlations between age (months) and PSP-specific GMTs (log 10 EU/mL). These correlations were strong for Ply ($R^2$=0.63434), PhtD ($R^2$=0.63297) and PhtE ($R^2$=0.59359) and weaker although significant for LytB ($R^2$=0.45824) and PcpA ($R^2$=0.31625). Assessing exposure-driven anti-PSP antibodies in children distributed in four even age groups ($\leq$17, 18-35, 36-49 and $\geq$50 months) indicated that anti-PcpA antibodies were already present at high titers in children <18 months (FIG. 1), their further increase with age being significant (p=0.022) but less marked than for other PSPs (p<0.001). Anti-PcpA and anti-PhtE antibodies were already present in the youngest infant, aged 2.6 months, presumably reflecting passive transfer of maternal antibodies.

Figure 2:
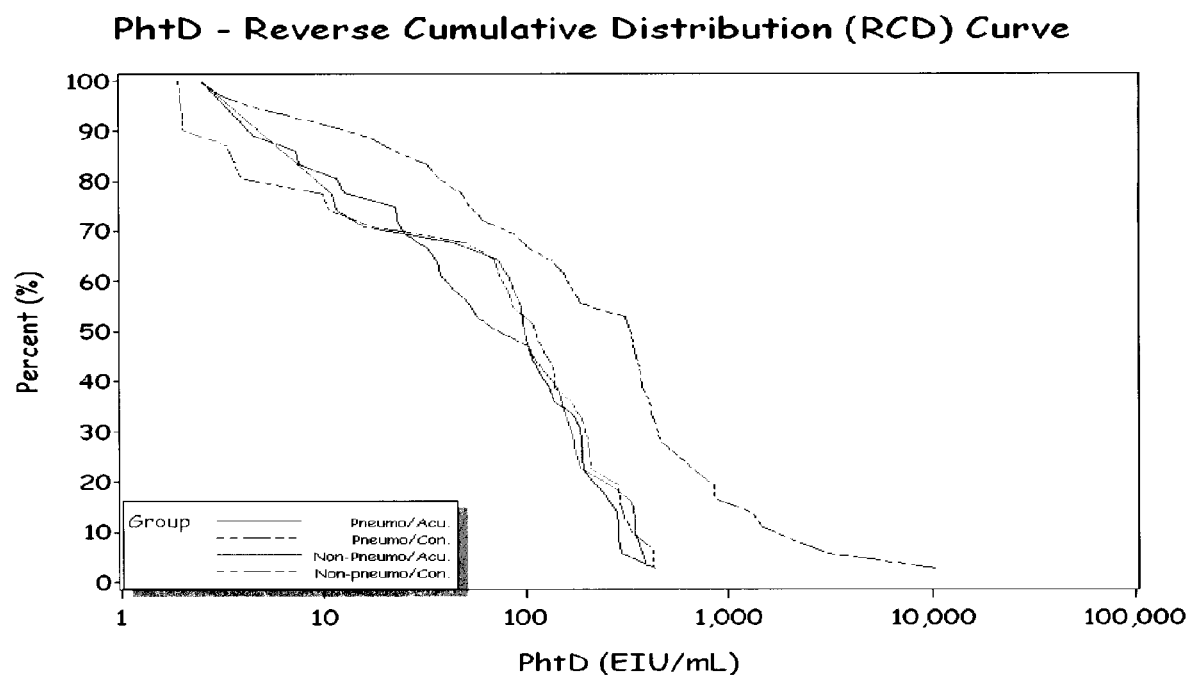
FIG. 2. Distribution of anti-PhtD IgG antibodies in children with pneumococcal or non-pneumococcal CAP.
Figure 3:
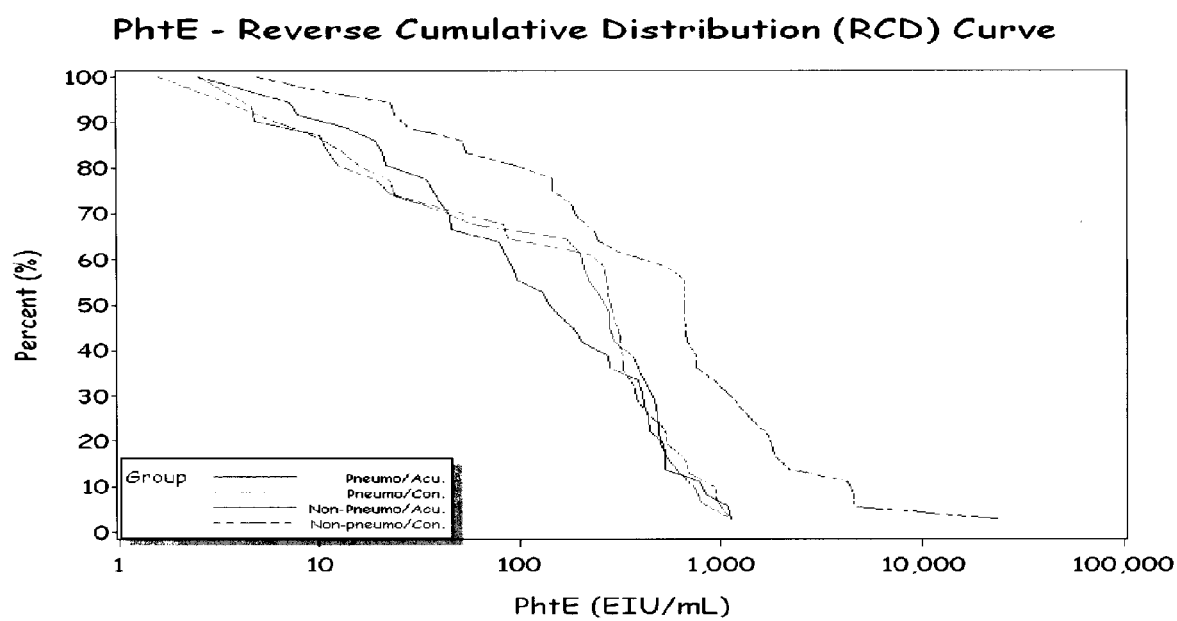
FIG. 3. Distribution of anti-PhtE IgG antibodies in children with pneumococcal or non-pneumococcal CAP.
Figure 4:
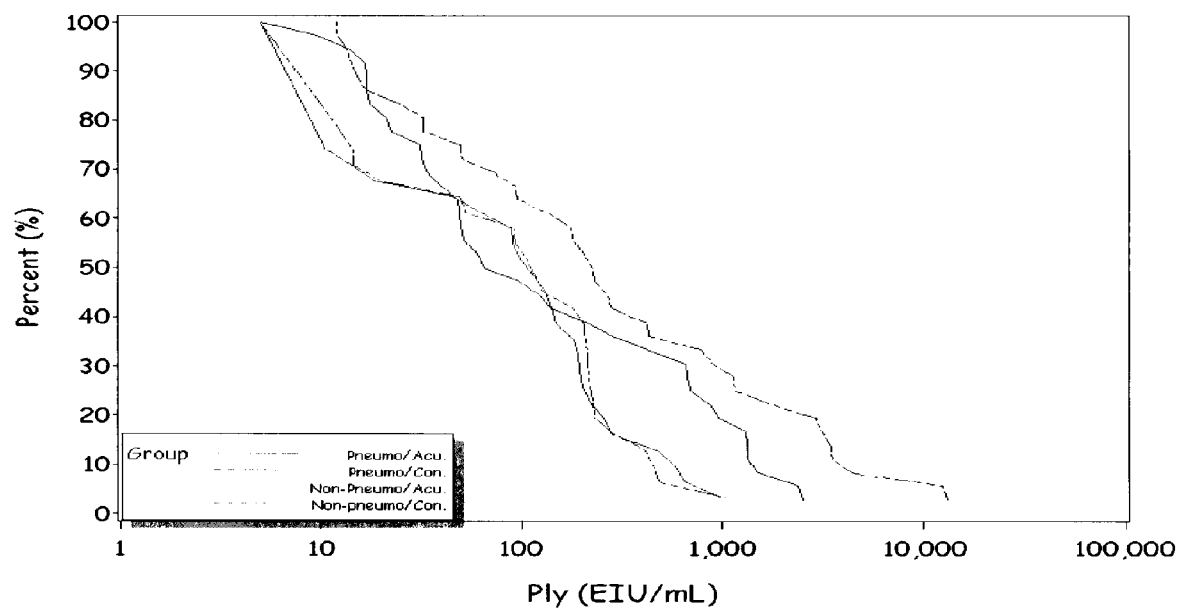
FIG. 4. Distribution of anti-Ply IgG antibodies in children with pneumococcal or non-pneumococcal CAP.
Figure 5:
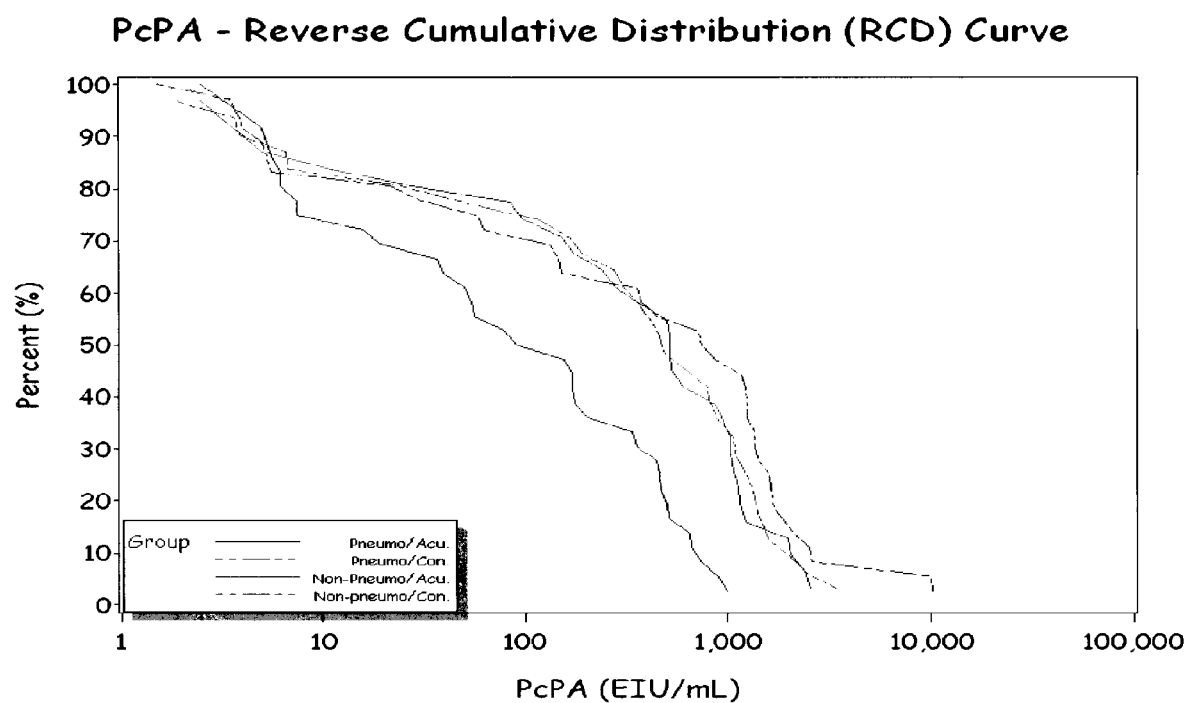
FIG. 5. Distribution of anti-PcPA IgG antibodies in children with pneumococcal or non-pneumococcal CAP.

The five PSP used in this study are well conserved (>95-98%) among pneumococcal strains. Should anti-PSP IgG antibodies play a role in protection against pneumococcal pneumonia, one might therefore expect to find differences in pneumococcal immunity between children with pneumococcal or non-pneumococcal CAP. At admission, antibodies to PhtD, PhtE and LytB were similar in P-CAP and NP-CAP children (Table 4 and FIG. 2), suggesting similar past exposure to *S. pneumoniae* and B cell response capacity. Anti-Ply at admission were significantly higher in P-CAP (446 EU/ml) than in NP-CAP (169 EU/ml, p=0.03) children. This difference essentially reflected a greater proportion of P-CAP children with high anti-Ply antibodies (>200 EU/ml; FIG. 2) at admission. In striking contrast, anti-PcpA antibodies at admission were 3-fold lower (233 vs 716 EU/ml, p=0.001) in children hospitalized for P-CAP than for NP-CAP, reflecting a greater proportion of NP-CAP children with anti-PcpA titers at any value >10 EU/ml (FIG. 2). Thus, preexisting antipneumococcal immunity differed significantly between children hospitalized with CAP of pneumococcal and non-pneumococcal origin.

Convalescent antibody titers were then compared, harvested 3 weeks after admission for P-CAP or NP-CAP. Convalescent antibody titers to Ply, PhtD, PhtE and Lyt-B remained significantly (p<0.01) influenced by age, which in contrast did not influence anti-PcpA convalescent titers. Anti-LytB antibodies were not increased at all in convalescent sera, indicating the low infection-induced immunogenicity of this antigen (Table 4; FIG. 2). Convalescent antibody titers to the four other PSP were higher in P-CAP than in NP-CAP patients. These differences only reached statistical significance for anti-Ply antibodies (Table 2). This is likely to essentially reflect the marked heterogeneity of seroresponses in relatively small study groups as the reverse distributing cumulative curves clearly indicate the higher proportion of moderate or high anti-PhtD and anti-PhtE titers in P-CAP children (FIG. 2). Interestingly, anti-PcpA antibodies which were 3-fold lower in P-CAP children at admission reached similar titers as in NP-CAP children only 3 weeks after a single episode of pneumonia.

Multivariate analyses confirmed high Ply antibodies (p=0.014) and low PcpA antibodies (p=0.004) at admission as the only significant predictors of pneumococcal versus non-pneumococcal pneumonia in hospitalized children, regardless of their age and clinical scores.

E. Data Analysis

The data demonstrates that the use of a panel of immunogenic PSPs significantly improves the diagnosis of pneumococcal infections in young children with clinical signs of pneumonia, as defined by the World Health Organization (WHO). WHO have identified anti-PcpA antibodies as a key diagnostic marker of pneumococcal CAP. These antibodies are detectable at much lower levels during the acute phase in children with pneumococcal rather than non-pneumococcal pneumonia.

In this study, we postulated that the sensitivity of PSP-based assays could be improved by the use of most immunogenic proteins and/or by their combination. The importance of PSP immunogenicity was largely confirmed by the demonstration of sensitivities ranging from 0.14 for LytB, to 0.44 for Ply, 0.56 for PhtD and 0.64 for either the PhtE or PcpA proteins. This ranking directly reflects the relative immunogenicity of PSP, as evidenced by a similar gradient of mean fold increase of antibody responses (LytB (1.51), Ply (2.15), PhtD (4.22), PcpA (5.62) and PhtE (6.88)) largely independent of age. More impressively, the combination of several PSP markedly increased assay sensitivity: combining anti-PcpA and anti-PhtE responses reached a sensitivity of 0.92 for the diagnosis of a recent pneumococcal exposure/infection in children hospitalized for CAP, which was increased to 0.94 by the addition of anti-Ply responses. One reason for these improved sensitivities, and their related negative predictive values, is that past colonization or infections did usually not elicit antibodies to all PSPs, such that high preexisting antibody titers to one PSP may not prevent responses to other antigens. Another reason is the identification of the PcpA protein as a key diagnostic marker of pneumococcal CAP: in its absence, assay sensitivity reached 0.67 rather than 0.92 regardless of the PSP combination tested (Table 2).

The use of a panel of five PSP as immunoprobes identified $^{34}/_{75}$ (45%) CAP children with evidence of acute pneumococcal responses. This included all patients with pneumococcal DNA in their blood (Ply$^+$-PCR), with two exceptions: anti-PSP responses remained negative in a less than 3 month-old infant hospitalized after a 4-day history of fever and cough. This suggests that serodiagnosis may remain difficult in very young infants experiencing their first exposure to $S.$ $pneumoniae$ at time of immune immaturity. As few young infants were enrolled in this study, this question will have to be addressed in subsequent studies. The other Ply$^+$-PCR child lacking anti-PSP responses was a pre-schooler with a prolonged history of cough (17 days) and fever (7 days) prior to admission for CAP. Her antibody titers were already very high at hospitalization (anti-Ply: 952 EU/ml, anti-PhtD: 192 EU/ml, anti-PhtE: 277 EU/ml, anti-PcpA: 462 EU/ml), indicating their activation prior to admission. To note, the serodiagnosis of this patient would have been considered as positive with less stringent study criteria than the exclusive use of fold-increase of antibody titers. Eight other children (mean age 44.5 months, range 22-66) had high preexisting immunity to ≧3 PSP at admission (anti-Ply>380 EU/ml, anti-PhtD>111 EU/ml, anti-PhtE>393 EU/ml and anti-PcpA>266 EU/ml), and were considered neither as P-CAP nor as NP-CAP patients to avoid attribution errors. Respiratory viruses (RSV, hMPV, parainfluenza, rhinovirus, adenovirus, enterovirus) were identified in all eight except one, who had evidence of $M.$ $pneumoniae$ infection, and all Ply-PCR remained negative. Including these 8 patients to the NP-CAP group would further increase the negative predictive value of each anti-PSP assay.

It cannot be concluded that some anti-PSP responses resulted from nasopharyngeal carriage. At admission, $S.$ $pneumoniae$ was more frequently identified in the nasopharynx of P-CAP than NP-CAP patients (44% versus 22%, p=0.06), in accordance with the fact that nasopharyngeal acquisition precedes pneumococcal disease. For instance, it is known that the acquisition of a new pneumococcal strain induces the development of antibodies to certain PSP such as Ply, PhtB and PhtE (Holmlund E, $PIDJ$ 2007). In contrast, pneumococcal carriage alone is not associated with acute seroresponses. Nasopharyngeal sampling prior to admission for CAP was not available to identify recent acquisition of carriage, and there are reasons to believe that anti-PcpA antibodies are not readily elicited through nasopharyngeal carriage acquisition (see below). AOM was diagnosed at admission in three NP-CAP and four P-CAP patients (NS), antibiotic prescription within 30 days being similar in both groups. Previous prospective studies on the etiology of CAP did not include formal control groups of healthy children or of patients suffering from other diseases. Interestingly, admission antibody titers of our 38 CAP patients aged 24-60 months (mean age 43.1 months, P-CAP:18, NP-CAP:18, indeterminate:2) were significantly lower than those of 58 healthy children (mean age 43.6 months) selected as controls with no history of previous lower respiratory tract infection for another study (Ply: 460 vs 745 EU/ml, PhtD: 150 vs 300 EU/ml, PhtE: 382 vs 679 EU/ml, PcpA: 580 vs 1440 EU/ml, respectively). It will thus be interesting to assess the influence of carriage acquisition, AOM and lower respiratory infections on PhtD, PhtE and PcpA immunity in prospective cohort studies.

The etiologic data presented herein corroborates well with findings of other investigators. The attributed role of $S.$ $pneumoniae$ was indeed documented in 44% of cases in a US study with a similar design, study population and extensive diagnostic workup (Michelow 2004). It is also in accordance with the 20-30% protective efficacy of a 7-valent pneumococcal conjugate vaccine. Should the high sensitivity and specificity of these PSP-based immunoprobes be confirmed in other settings, the same could thus prove extremely useful for the evaluation of the pediatric pneumococcal disease burden. Indeed, a pneumococcal etiology may not be solely derived from clinical symptoms, as confirmed again here. Increasing the sensitivity of the diagnosis of pneumococcal CAP would also greatly reduce the size of the studies required to demonstrate pneumococcal vaccine efficacy in various country settings.

It was also observed that anti-pneumococcal immunity at admission was significantly different in children admitted with pneumococcal versus non-pneumococcal CAP. PSP-specific antibodies were found in all children, over a wide range of concentrations reflecting age and past-exposure. Admission antibody levels to PhtD, PhtE and Lyt-B were similar in both groups, supporting the claim that these children were otherwise healthy children who had been previously exposed to $S.$ $pneumoniae$, with the possible exception of the youngest infants in whom antibodies may have been of maternal origin. At admission, anti-Ply IgG antibodies were ≧2-fold higher in P-CAP children. This significant difference essentially reflected a greater proportion of P-CAP children with high anti-Ply antibodies (>200 EU/ml; FIG. 2) already at admission. Thus, Ply-specific responses were more rapidly induced in children with P-CAP than responses to other PSP. It is tempting to postulate that anti-Ply immunity had been previously induced in these patients, allowing rapid anamnestic responses at time of pneumococcal infection. The observation of higher admission anti-Ply antibodies is in accordance with the findings of others and supports the inclusion of "high" anti-Ply titers in the serologic diagnostic criteria of pneumococcal CAP.

In striking contrast, anti-PcpA antibodies were 3-fold lower in children admitted for pneumococcal CAP, a difference which was highly significant (p=0.001). This is because saliva has the highest in vivo concentration of Mn2+ (36 µM), such that PcpA expression is repressed unless pneumococci invade the lung or bloodstream, where the levels of Mn2+ are 1.000-fold lower (20 nM). As PcpA is not expressed during nasopharyngeal colonization, anti-PcpA responses reflect pneumococcal disease rather than colonization. This may contribute to the unique sensitivity of the PcpA-based assay (Table 3), which avoids confusion with nasopharyngeal-elicited responses. This PcpA expression pattern has another implication: children with preexisting anti-PcpA immunity are those in whom pneumococcal disease has occurred previously. Conversely, low anti-PcpA antibody titers at time of admission for CAP indicate that children may undergo a primary episode of pneumococcal disease—which could be associated with a higher risk of lower respiratory disease. PcpA antibodies may be just a marker of the protective immunity raised by previous disease. In any case, PcpA appears to play a critical role in establishing pneumococcal pneumonia and, therefore, needs to be further assessed as a potential vaccine or diagnostic component.

In summary, a panel of five pneumococcal surface proteins (PSP) was used to identify pneumococcal infection in a prospective study of 75 young children (mean age 33.7 months) hospitalized with CAP. Twenty-three (31%) patients had either a positive pneumolysin (Ply) blood PCR (20%), or a $\geq$2-fold increase of anti-Ply antibodies (21%). Adding PhtD, PhtE, LytB and PcpA as immunological probes identified 36/75 (45%) patients with acute pneumococcal infection (P-CAP), increasing the sensitivity of the diagnosis from 0.44 (Ply alone) to 0.94. Neither age, gender, WHO scores for clinical severity, duration of cough/fever or prior antibiotic use distinguished these 36 patients from 31 children with no evidence of recent pneumococcal exposure (NP-CAP). At admission, antibodies to PhtD, PhtE and Lyt-B were similar in both groups, whereas anti-Ply antibodies were significantly higher in P-CAP patients than in NP-CAP patients (446 vs 169 EU/ml, respectively; p=0.031). In contrast, P-CAP children had three-fold lower anti-PcpA antibodies (233 vs 716 EU/ml, p=0.001). Multivariate analyses confirmed low PcpA antibodies at time of admission as the most significant predictor (p=0.004) of P-CAP in young children, in accordance with the preferential expression of PcpA in low $Mn^{2+}$ compartments such as the lung rather than the nasopharynx.

All references cited herein are hereby incorporated by reference in their entirety into this disclosure. While the present invention has been described in terms of the preferred embodiments, it is understood that variations and modifications will occur to those skilled in the art. Therefore, it is intended that the appended claims cover all such equivalent variations that come within the scope of the invention as claimed.

TABLE 1

Convalescent responses to surface pneumococcal proteins

|  | Responders ($\geq$2-fold) (N/%) | Mean (EU/ml) | 95% CI (EU/ml) | GMT | Range (EU/ml) | Sensitivity | NPV |
| --- | --- | --- | --- | --- | --- | --- | --- |
| Ply | 16/75 (21%) | 895 | (389-1401) | 154.33 | ND-13079 | 0.44 | 0.61 |
| PhtD | 20/75 (27%) | 436 | (147-723) | 107.48 | ND-10287 | 0.56 | 0.66 |
| PhtE | 24/75 (32%) | 978 | (302-1654) | 241.89 | ND-24877 | 0.64 | 0.70 |
| LytB | 5/75 (7%) | 37 | (25-49) | 23.94 | ND-439 | 0.14 | 0.50 |
| PcpA | 23/74 (31%) | 1062 | (668-1456) | 281.04 | ND-10226 | 0.64 | 0.70 |

ND: below detection level; 95% CI: 95% Confidence interval; GMT: geometric mean titers NPV: negative predictive value

TABLE 2

Sensitivities of the combination of anti-PSP responses for the diagnosis of pneumococcal CAP

|  | Ply | PhtD | PhtE | PcpA | LytB |
| --- | --- | --- | --- | --- | --- |
| Ply | 0.44 | 0.58 | 0.67 | 0.86 | 0.47 |
| PhtD | 0.58 | 0.56 | 0.67 | 0.89 | 0.61 |
| PhtE | 0.67 | 0.67 | 0.64 | 0.92 | 0.67 |
| PcpA | 0.86 | 0.89 | 0.92 | 0.64 | 0.72 |
| LytB | 0.47 | 0.61 | 0.67 | 0.67 | 0.14 |

TABLE 3

Exposure-driven serum IgG antibodies to surface pneumococcal proteins

|  | Seropositivity* N/% | GMT (EU/ml) | 95% CI (EU/ml) | GMT | Range (EU/ml) |
| --- | --- | --- | --- | --- | --- |
| Ply | 67/75 (89%) | 498 | (233-763) | 110.59 | ND-8790 |
| PhtD | 64/75 (85%) | 140 | (109-171) | 59.94 | ND-604 |
| PhtE | 71/75 (95%) | 326 | (249-403) | 130.03 | ND-1561 |
| LytB | 73/75 (97%) | 30 | (24-36) | 21.79 | ND-120 |
| PcpA | 69/74 (93%) | 515 | (375-655) | 148.36 | ND-2563 |

ND: below detection level;
95% CI: 95% Confidence interval;
GMT: geometric mean titers
*Defined as $\geq$ 5 EU/ml

TABLE 4

Anti-PSP antibodies in children with CAP of pneumococcal versus non-pneumococcal origin

| PSP | Stage | NP-CAP (n=31) | | | P-CAP (n=36) | | | P value |
| --- | --- | --- | --- | --- | --- | --- | --- | --- |
| | | Mean (EU/ml) | 95% CI | GMT | Mean (EU/ml) | 95% CI | GMT | (P- vs NP-CAP) |
| Ply | Acute | 169 | (86-252) | 58.34 | 446 | (220-672) | 115.8 | 0.031 |
| PhtD | Acute | 125 | (80-170) | 49.61 | 112 | (74-150) | 50.16 | 0.637 |
| PhtE | Acute | 291 | (190-392) | 110.22 | 264 | (161-367) | 104.26 | 0.712 |
| PcpA | Acute | 716 | (442-990) | 241.67 | 233 | (138-328) | 66.64 | 0.001 |
| LytB | Acute | 31 | (21-41) | 22.16 | 24 | (18-30) | 18.61 | 0.183 |
| Ply | Convalescent | 165 | (86-244) | 58.82 | 1433 | (409-2457) | 235.13 | 0.023 |
| PhtD | Convalescent | 132 | (85-179) | 49.39 | 725 | (129-1321) | 170.54 | 0.066 |
| PhtE | Convalescent | 307 | (195-419) | 105.43 | 1615 | (204-3026) | 395.41 | 0.086 |
| PcpA | Convalescent | 759 | (456-1062) | 247.13 | 1308 | (534-2082) | 247.98 | 0.216 |
| LytB | Convalescent | 28 | (20-36) | 19.9 | 42 | (17-67) | 24.72 | 0.291 |

PSP: Pneumococcal surface proteins
NP-CAP: Community-Acquired Pneumonia without evidence of acute pneumococcal infection
P-CAP: Community-Acquired Pneumonia with evidence of acute pneumococcal infection
95% CI: 95% confidence interval
GMT: geometric mean liters

What is claimed is:

1. A method of diagnosing pneumonia or an infection by *Streptococcus pneumoniae* in a subject comprising:
   a) contacting a biological sample of the subject with PcpA, PhtD, PhtE, LytB and Ply antigens; and
   b) detecting complexes formed between antibodies in the biological sample and at least two of the PcpA, PhtD, PhtE, LytB and Ply antigens;
   wherein detection of at least two complexes in step b) is indicative of infection by *Streptococcus pneumoniae* in the subject.

2. The method of claim 1 wherein detecting the formation of an antigen-antibody complex comprises detecting human immunoglobulin in the antigen-antibody complex.

3. The method of claim 2 wherein detecting human immunoglobulin comprises contacting the antigen-antibody complex with a second antibody that binds to human immunoglobulin for a time and under conditions sufficient for said second antibody to bind to the human immunoglobulin in the complex and then detecting the bound anti-human immunoglobulin.

4. The method of claim 2 wherein the second antibody is labeled with a detectable marker or reporter molecule.

5. A method for determining the response of a subject having pneumonia or an infection by *Streptococcus pneumoniae* to treatment with a therapeutic compound for said pneumonia or infection, said method comprising:
   a) contacting a biological sample of the subject with PcpA, PhtD, PhtE, LytB and Ply antigens; and
   b) detecting complexes formed between antibodies in the biological sample and at least two of the PcpA, PhtD, PhtE, LytB and Ply antigens;
   c) determining if the amount of the complexes detected is increased, unchanged or decreased in a biological sample of the subject obtained prior to treatment;
   wherein an unchanged or decreased amount of the complexes detected after treatment indicates that the subject is responding to treatment.

6. The method of claim 5 comprising contacting the biological sample with the antigens for a time and under conditions sufficient for an antigen-antibody complex to form and then detecting the formation of an antigen-antibody complex.

7. The method of claim 6 wherein detecting the formation of an antigen-antibody complex comprises detecting human immunoglobulin in the antigen-antibody complex.

8. The method of claim 7 wherein detecting human immunoglobulin comprises contacting the antigen-antibody complex with a second antibody that binds to human immunoglobulin for a time and under conditions sufficient for said second antibody to bind to the human immunoglobulin in the complex and then detecting the bound anti-human immunoglobulin.

9. The method of claim 8 wherein the second antibody is labeled with a detectable marker or reporter molecule.

10. The method of claim 6 comprising performing an enzyme-linked immunosorbent assay (ELISA).

11. The method of claim 10 wherein the ELISA is a sandwich ELISA using a capture antibody and a detection antibody.

12. A method of diagnosing infection by *Streptococcus pneumoniae* in a subject comprising contacting a biological sample comprising an antibody with a solid matrix comprising PcpA, PhtD, PhtE, LytB and Ply antigens under conditions suitable for antibodies reactive to two or more of the antigens to bind thereto, and detecting the binding of said antibody to at least two of said antigens, wherein detection of antibodies reactive to said antigens indicates the subject is infected by *Streptococcus pneumoniae*.

* * * * *

SEQUENCE LISTING

<160> NUMBER OF SEQ ID NOS: 8

<210> SEQ ID NO 1
<211> LENGTH: 471
<212> TYPE: PRT
<213> ORGANISM: Streptococcus pneumoniae

<400> SEQUENCE: 1

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
            85                  90                  95

Met Thr Tyr Ser Ile Asp Leu Pro Gly Leu Ala Ser Ser Asp Ser Phe
        100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Val
        130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
```

```
                    210                 215                 220
Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
                275                 280                 285

Ala Val Ile Leu Gly Gly Asp Pro Ser Ser Gly Ala Arg Val Val Thr
                290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
                355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
                435                 440                 445

Arg Lys Arg Thr Ile Ser Ile Trp Gly Thr Thr Leu Tyr Pro Gln Val
                450                 455                 460

Glu Asp Lys Val Glu Asn Asp
465                 470

<210> SEQ ID NO 2
<211> LENGTH: 839
<212> TYPE: PRT
<213> ORGANISM: Streptococcus pneumoniae

<400> SEQUENCE: 2

Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
                20                  25                  30

Lys Lys Glu Ser Asn Arg Val Ser Tyr Ile Asp Gly Asp Gln Ala Gly
            35                  40                  45

Gln Lys Ala Glu Asn Leu Thr Pro Asp Glu Val Ser Lys Arg Glu Gly
        50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Ile Ile Ser Glu Glu Leu Leu Met Lys Asp Pro Asn Tyr Gln
                100                 105                 110

Leu Lys Asp Ser Asp Ile Val Asn Glu Ile Lys Gly Gly Tyr Val Ile
```

```
              115                 120                 125
Lys Val Asp Gly Lys Tyr Tyr Val Tyr Leu Lys Asp Ala Ala His Ala
130                 135                 140

Asp Asn Ile Arg Thr Lys Glu Glu Ile Lys Arg Gln Lys Gln Glu His
145                 150                 155                 160

Ser His Asn His Gly Gly Ser Asn Asp Gln Ala Val Val Ala Ala
                165                 170                 175

Arg Ala Gln Gly Arg Tyr Thr Thr Asp Asp Gly Tyr Ile Phe Asn Ala
                180                 185                 190

Ser Asp Ile Ile Glu Asp Thr Gly Asp Ala Tyr Ile Val Pro His Gly
                195                 200                 205

Asp His Tyr His Tyr Ile Pro Lys Asn Glu Leu Ser Ala Ser Glu Leu
                210                 215                 220

Ala Ala Ala Glu Ala Tyr Trp Asn Gly Lys Gln Gly Ser Arg Pro Ser
225                 230                 235                 240

Ser Ser Ser Ser Tyr Asn Ala Asn Pro Ala Gln Pro Arg Leu Ser Glu
                245                 250                 255

Asn His Asn Leu Thr Val Thr Pro Thr Tyr His Gln Asn Gln Gly Glu
                260                 265                 270

Asn Ile Ser Ser Leu Leu Arg Glu Leu Tyr Ala Lys Pro Leu Ser Glu
                275                 280                 285

Arg His Val Glu Ser Asp Gly Leu Ile Phe Asp Pro Ala Gln Ile Thr
                290                 295                 300

Ser Arg Thr Ala Arg Gly Val Ala Val Pro His Gly Asn His Tyr His
305                 310                 315                 320

Phe Ile Pro Tyr Glu Gln Met Ser Glu Leu Glu Lys Arg Ile Ala Arg
                325                 330                 335

Ile Ile Pro Leu Arg Tyr Arg Ser Asn His Trp Val Pro Asp Ser Arg
                340                 345                 350

Pro Glu Gln Pro Ser Pro Gln Ser Thr Pro Glu Pro Ser Pro Ser Pro
                355                 360                 365

Gln Pro Ala Pro Asn Pro Gln Pro Ala Pro Ser Asn Pro Ile Asp Glu
                370                 375                 380

Lys Leu Val Lys Glu Ala Val Arg Lys Val Gly Asp Gly Tyr Val Phe
385                 390                 395                 400

Glu Glu Asn Gly Val Ser Arg Tyr Ile Pro Ala Lys Asp Leu Ser Ala
                405                 410                 415

Glu Thr Ala Ala Gly Ile Asp Ser Lys Leu Ala Lys Gln Glu Ser Leu
                420                 425                 430

Ser His Lys Leu Gly Ala Lys Lys Thr Asp Leu Pro Ser Ser Asp Arg
                435                 440                 445

Glu Phe Tyr Asn Lys Ala Tyr Asp Leu Leu Ala Arg Ile His Gln Asp
                450                 455                 460

Leu Leu Asp Asn Lys Gly Arg Gln Val Asp Phe Glu Ala Leu Asp Asn
465                 470                 475                 480

Leu Leu Glu Arg Leu Lys Asp Val Pro Ser Asp Lys Val Lys Leu Val
                485                 490                 495

Asp Asp Ile Leu Ala Phe Leu Ala Pro Ile Arg His Pro Glu Arg Leu
                500                 505                 510

Gly Lys Pro Asn Ala Gln Ile Thr Tyr Thr Asp Asp Glu Ile Gln Val
                515                 520                 525

Ala Lys Leu Ala Gly Lys Tyr Thr Thr Glu Asp Gly Tyr Ile Phe Asp
530                 535                 540
```

```
Pro Arg Asp Ile Thr Ser Asp Glu Gly Asp Ala Tyr Val Thr Pro His
545                 550                 555                 560

Met Thr His Ser His Trp Ile Lys Lys Asp Ser Leu Ser Glu Ala Glu
                565                 570                 575

Arg Ala Ala Gln Ala Tyr Ala Lys Glu Lys Gly Leu Thr Pro Pro
            580                 585                 590

Ser Thr Asp His Gln Asp Ser Gly Asn Thr Glu Ala Lys Gly Ala Glu
            595                 600                 605

Ala Ile Tyr Asn Arg Val Lys Ala Lys Val Pro Leu Asp Arg
            610                 615                 620

Met Pro Tyr Asn Leu Gln Tyr Thr Val Glu Val Lys Asn Gly Ser Leu
625                 630                 635                 640

Ile Ile Pro His Tyr Asp His Tyr His Asn Ile Lys Phe Glu Trp Phe
                645                 650                 655

Asp Glu Gly Leu Tyr Glu Ala Pro Lys Gly Tyr Thr Leu Glu Asp Leu
                660                 665                 670

Leu Ala Thr Val Lys Tyr Tyr Val Glu His Pro Asn Glu Arg Pro His
            675                 680                 685

Ser Asp Asn Gly Phe Gly Asn Ala Ser Asp His Val Arg Lys Asn Lys
690                 695                 700

Val Asp Gln Asp Ser Lys Pro Asp Glu Asp Lys Glu His Asp Glu Val
705                 710                 715                 720

Ser Glu Pro Thr His Pro Glu Ser Asp Glu Lys Glu Asn His Ala Gly
                725                 730                 735

Leu Asn Pro Ser Ala Asp Asn Leu Tyr Lys Pro Ser Asp Thr Glu
            740                 745                 750

Glu Thr Glu Glu Glu Ala Glu Asp Thr Thr Asp Glu Ala Glu Ile Pro
            755                 760                 765

Gln Val Glu Asn Ser Val Ile Asn Ala Lys Ile Ala Asp Ala Glu Ala
            770                 775                 780

Leu Leu Glu Lys Val Thr Asp Pro Ser Ile Arg Gln Asn Ala Met Glu
785                 790                 795                 800

Thr Leu Thr Gly Leu Lys Ser Ser Leu Leu Gly Thr Lys Asp Asn
                805                 810                 815

Asn Thr Ile Ser Ala Glu Val Asp Ser Leu Leu Ala Leu Leu Lys Glu
            820                 825                 830

Ser Gln Pro Ala Pro Ile Gln
            835

<210> SEQ ID NO 3
<211> LENGTH: 1039
<212> TYPE: PRT
<213> ORGANISM: Streptococcus pneumoniae

<400> SEQUENCE: 3

Met Lys Phe Ser Lys Lys Tyr Ile Ala Ala Gly Ser Ala Val Ile Val
1               5                   10                  15

Ser Leu Ser Leu Cys Ala Tyr Ala Leu Asn Gln His Arg Ser Gln Glu
            20                  25                  30

Asn Lys Asp Asn Asn Arg Val Ser Tyr Val Asp Gly Ser Gln Ser Ser
            35                  40                  45

Gln Lys Ser Glu Asn Leu Thr Pro Asp Gln Val Ser Gln Lys Glu Gly
        50                  55                  60

Ile Gln Ala Glu Gln Ile Val Ile Lys Ile Thr Asp Gln Gly Tyr Val
65                  70                  75                  80
```

-continued

```
Thr Ser His Gly Asp His Tyr His Tyr Tyr Asn Gly Lys Val Pro Tyr
                85                  90                  95
Asp Ala Leu Phe Ser Glu Glu Leu Leu Met Lys Asp Pro Asn Tyr Gln
            100                 105                 110
Leu Lys Asp Ala Asp Ile Val Asn Glu Val Lys Gly Gly Tyr Ile Ile
        115                 120                 125
Lys Val Asp Gly Lys Tyr Tyr Val Tyr Leu Lys Asp Ala Ala His Ala
    130                 135                 140
Asp Asn Val Arg Thr Lys Asp Glu Ile Asn Arg Gln Lys Gln Glu His
145                 150                 155                 160
Val Lys Asp Asn Glu Lys Val Asn Ser Asn Val Ala Val Ala Arg Ser
                165                 170                 175
Gln Gly Arg Tyr Thr Thr Asn Asp Gly Tyr Val Phe Asn Pro Ala Asp
            180                 185                 190
Ile Ile Glu Asp Thr Gly Asn Ala Tyr Ile Val Pro His Gly Gly His
        195                 200                 205
Tyr His Tyr Ile Pro Lys Ser Asp Leu Ser Ala Ser Glu Leu Ala Ala
    210                 215                 220
Ala Lys Ala His Leu Ala Gly Lys Asn Met Gln Pro Ser Gln Leu Ser
225                 230                 235                 240
Tyr Ser Ser Thr Ala Ser Asp Asn Asn Thr Gln Ser Val Ala Lys Gly
                245                 250                 255
Ser Thr Ser Lys Pro Ala Asn Lys Ser Glu Asn Leu Gln Ser Leu Leu
            260                 265                 270
Lys Glu Leu Tyr Asp Ser Pro Ser Ala Gln Arg Tyr Ser Glu Ser Asp
        275                 280                 285
Gly Leu Val Phe Asp Pro Ala Lys Ile Ile Ser Arg Thr Pro Asn Gly
    290                 295                 300
Val Ala Ile Pro His Gly Asp His Tyr His Phe Ile Pro Tyr Ser Lys
305                 310                 315                 320
Leu Ser Ala Leu Glu Glu Lys Ile Ala Arg Met Val Pro Ile Ser Gly
                325                 330                 335
Thr Gly Ser Thr Val Ser Thr Asn Ala Lys Pro Asn Glu Val Val Ser
            340                 345                 350
Ser Leu Gly Ser Leu Ser Ser Asn Pro Ser Ser Leu Thr Thr Ser Lys
        355                 360                 365
Glu Leu Ser Ser Ala Ser Asp Gly Tyr Ile Phe Asn Pro Lys Asp Ile
    370                 375                 380
Val Glu Glu Thr Ala Thr Ala Tyr Ile Val Arg His Gly Asp His Phe
385                 390                 395                 400
His Tyr Ile Pro Lys Ser Asn Gln Ile Gly Gln Pro Thr Leu Pro Asn
                405                 410                 415
Asn Ser Leu Ala Thr Pro Ser Pro Ser Leu Pro Ile Asn Pro Gly Thr
            420                 425                 430
Ser His Glu Lys His Glu Glu Asp Gly Tyr Gly Phe Asp Ala Asn Arg
        435                 440                 445
Ile Ile Ala Glu Asp Glu Ser Gly Phe Val Met Ser His Gly Asp His
    450                 455                 460
Asn His Tyr Phe Phe Lys Lys Asp Leu Thr Glu Glu Gln Ile Lys Ala
465                 470                 475                 480
Ala Gln Lys His Leu Glu Glu Val Lys Thr Ser His Asn Gly Leu Asp
                485                 490                 495
Ser Leu Ser Ser His Glu Gln Asp Tyr Pro Ser Asn Ala Lys Glu Met
            500                 505                 510
```

```
Lys Asp Leu Asp Lys Lys Ile Glu Glu Lys Ile Ala Gly Ile Met Lys
        515                 520                 525

Gln Tyr Gly Val Lys Arg Glu Ser Ile Val Val Asn Lys Glu Lys Asn
        530                 535                 540

Ala Ile Ile Tyr Pro His Gly Asp His His Ala Asp Pro Ile Asp
545                 550                 555                 560

Glu His Lys Pro Val Gly Ile Gly His Ser His Ser Asn Tyr Glu Leu
                565                 570                 575

Phe Lys Pro Glu Glu Gly Val Ala Lys Lys Glu Gly Asn Lys Val Tyr
            580                 585                 590

Thr Gly Glu Glu Leu Thr Asn Val Val Asn Leu Leu Lys Asn Ser Thr
        595                 600                 605

Phe Asn Asn Gln Asn Phe Thr Leu Ala Asn Gly Gln Lys Arg Val Ser
        610                 615                 620

Phe Ser Phe Pro Pro Glu Leu Glu Lys Lys Leu Gly Ile Asn Met Leu
625                 630                 635                 640

Val Lys Leu Ile Thr Pro Asp Gly Lys Val Leu Glu Lys Val Ser Gly
                645                 650                 655

Lys Val Phe Gly Glu Gly Val Gly Asn Ile Ala Asn Phe Glu Leu Asp
            660                 665                 670

Gln Pro Tyr Leu Pro Gly Gln Thr Phe Lys Tyr Thr Ile Ala Ser Lys
        675                 680                 685

Asp Tyr Pro Glu Val Ser Tyr Asp Gly Thr Phe Thr Val Pro Thr Ser
        690                 695                 700

Leu Ala Tyr Lys Met Ala Ser Gln Thr Ile Phe Tyr Pro Phe His Ala
705                 710                 715                 720

Gly Asp Thr Tyr Leu Arg Val Asn Pro Gln Phe Ala Val Pro Lys Gly
                725                 730                 735

Thr Asp Ala Leu Val Arg Val Phe Asp Glu Phe His Gly Asn Ala Tyr
            740                 745                 750

Leu Glu Asn Asn Tyr Lys Val Gly Glu Ile Lys Leu Pro Ile Pro Lys
        755                 760                 765

Leu Asn Gln Gly Thr Thr Arg Thr Ala Gly Asn Lys Ile Pro Val Thr
        770                 775                 780

Phe Met Ala Asn Ala Tyr Leu Asp Asn Gln Ser Thr Tyr Ile Val Glu
785                 790                 795                 800

Val Pro Ile Leu Glu Lys Glu Asn Gln Thr Asp Lys Pro Ser Ile Leu
                805                 810                 815

Pro Gln Phe Lys Arg Asn Lys Ala Gln Glu Asn Leu Lys Leu Asp Glu
            820                 825                 830

Lys Val Glu Glu Pro Lys Thr Ser Glu Lys Val Glu Lys Glu Lys Leu
        835                 840                 845

Ser Glu Thr Gly Asn Ser Thr Ser Asn Ser Thr Leu Glu Glu Val Pro
        850                 855                 860

Thr Val Asp Pro Val Gln Glu Lys Val Ala Lys Phe Ala Glu Ser Tyr
865                 870                 875                 880

Gly Met Lys Leu Glu Asn Val Leu Phe Asn Met Asp Gly Thr Ile Glu
                885                 890                 895

Leu Tyr Leu Pro Ser Gly Glu Val Ile Lys Lys Asn Met Ala Asp Phe
            900                 905                 910

Thr Gly Glu Ala Pro Gln Gly Asn Gly Glu Asn Lys Pro Ser Glu Asn
        915                 920                 925

Gly Lys Val Ser Thr Gly Thr Val Glu Asn Gln Pro Thr Glu Asn Lys
```

```
                    930              935              940
Pro Ala Asp Ser Leu Pro Glu Ala Pro Asn Glu Lys Pro Val Lys Pro
945                 950                  955                 960

Glu Asn Ser Thr Asp Asn Gly Met Leu Asn Pro Glu Gly Asn Val Gly
                965                  970                 975

Ser Asp Pro Met Leu Asp Pro Ala Leu Glu Glu Ala Pro Ala Val Asp
                980                  985                 990

Pro Val Gln Glu Lys Leu Glu Lys Phe Thr Ala Ser Tyr Gly Leu Gly
                995                 1000                1005

Leu Asp Ser Val Ile Phe Asn Met Asp Gly Thr Ile Glu Leu Arg
         1010                 1015                1020

Leu Pro Ser Gly Glu Val Ile Lys Lys Asn Leu Ser Asp Leu Ile
         1025                 1030                1035

Ala

<210> SEQ ID NO 4
<211> LENGTH: 677
<212> TYPE: PRT
<213> ORGANISM: Streptococcus pneumoniae

<400> SEQUENCE: 4

Met Asn Leu Gly Glu Phe Trp Tyr Asn Lys Ile Asn Lys Asn Arg Gly
1               5                   10                  15

Arg Arg Leu Met Lys Lys Val Arg Phe Ile Phe Leu Ala Leu Leu Phe
                20                  25                  30

Phe Leu Ala Ser Pro Glu Gly Ala Met Ala Ser Asp Gly Thr Trp Gln
            35                  40                  45

Gly Lys Gln Tyr Leu Lys Glu Asp Gly Ser Gln Ala Ala Asn Glu Trp
        50                  55                  60

Val Phe Asp Thr His Tyr Gln Ser Trp Phe Tyr Ile Lys Ala Asp Ala
65                  70                  75                  80

Asn Tyr Ala Glu Asn Glu Trp Leu Lys Gln Gly Asp Asp Tyr Phe Tyr
                85                  90                  95

Leu Lys Ser Gly Gly Tyr Met Ala Lys Ser Glu Trp Val Glu Asp Lys
            100                 105                 110

Gly Ala Phe Tyr Tyr Leu Asp Gln Asp Gly Lys Met Lys Arg Asn Ala
        115                 120                 125

Trp Val Gly Thr Ser Tyr Val Gly Ala Thr Gly Ala Lys Val Ile Glu
130                 135                 140

Asp Trp Val Tyr Asp Ser Gln Tyr Asp Ala Trp Phe Tyr Ile Lys Ala
145                 150                 155                 160

Asp Gly Gln His Ala Glu Lys Glu Trp Leu Gln Ile Lys Gly Lys Asp
                165                 170                 175

Tyr Tyr Phe Lys Ser Gly Gly Tyr Leu Leu Thr Ser Gln Trp Ile Asn
            180                 185                 190

Gln Ala Tyr Val Asn Ala Ser Gly Ala Lys Val Gln Gln Gly Trp Leu
        195                 200                 205

Phe Asp Lys Gln Tyr Gln Ser Trp Phe Tyr Ile Lys Glu Asn Gly Asn
            210                 215                 220

Tyr Ala Asp Lys Glu Trp Ile Phe Glu Asn Gly His Tyr Tyr Tyr Leu
225                 230                 235                 240

Lys Ser Gly Gly Tyr Met Ala Ala Asn Glu Trp Ile Trp Asp Lys Glu
                245                 250                 255

Ser Trp Phe Tyr Leu Lys Phe Asp Gly Lys Met Ala Glu Lys Glu Trp
            260                 265                 270
```

```
Val Tyr Asp Ser His Ser Gln Ala Trp Tyr Tyr Phe Lys Ser Gly Gly
            275                 280                 285

Tyr Met Thr Ala Asn Glu Trp Ile Trp Asp Lys Glu Ser Trp Phe Tyr
        290                 295                 300

Leu Lys Ser Asp Gly Lys Ile Ala Glu Lys Trp Val Tyr Asp Ser
305                 310                 315                 320

His Ser Gln Ala Trp Tyr Tyr Phe Lys Ser Gly Gly Tyr Met Thr Ala
                325                 330                 335

Asn Glu Trp Ile Trp Asp Lys Glu Ser Trp Phe Tyr Leu Lys Ser Asp
            340                 345                 350

Gly Lys Ile Ala Glu Lys Glu Trp Val Tyr Asp Ser His Ser Gln Ala
            355                 360                 365

Trp Tyr Tyr Phe Lys Ser Gly Gly Tyr Met Ala Lys Asn Glu Thr Val
        370                 375                 380

Asp Gly Tyr Gln Leu Gly Ser Asp Gly Lys Trp Leu Gly Gly Lys Thr
385                 390                 395                 400

Thr Asn Glu Asn Ala Ala Tyr Tyr Gln Val Val Pro Val Thr Ala Asn
                405                 410                 415

Val Tyr Asp Ser Asp Gly Glu Lys Leu Ser Tyr Ile Ser Gln Gly Ser
            420                 425                 430

Val Val Trp Leu Asp Lys Asp Arg Lys Ser Asp Lys Arg Leu Ala
        435                 440                 445

Ile Thr Ile Ser Gly Leu Ser Gly Tyr Met Lys Thr Glu Asp Leu Gln
        450                 455                 460

Ala Leu Asp Ala Ser Lys Asp Phe Ile Pro Tyr Tyr Glu Ser Asp Gly
465                 470                 475                 480

His Arg Phe Tyr His Tyr Val Ala Gln Asn Ala Ser Ile Pro Val Ala
                485                 490                 495

Ser His Leu Ser Asp Met Glu Val Gly Lys Lys Tyr Tyr Ser Ala Asp
            500                 505                 510

Gly Leu His Phe Asp Gly Phe Lys Leu Glu Asn Pro Phe Leu Phe Lys
            515                 520                 525

Asp Leu Thr Glu Ala Thr Asn Tyr Ser Ala Glu Glu Leu Asp Lys Val
            530                 535                 540

Phe Ser Leu Leu Asn Ile Asn Asn Ser Leu Leu Glu Asn Lys Gly Ala
545                 550                 555                 560

Thr Phe Lys Glu Ala Glu Glu His Tyr His Ile Asn Ala Leu Tyr Leu
                565                 570                 575

Leu Ala His Ser Ala Leu Glu Ser Asn Trp Gly Arg Ser Lys Ile Ala
            580                 585                 590

Lys Asp Lys Asn Asn Phe Phe Gly Ile Thr Ala Tyr Asp Thr Thr Pro
        595                 600                 605

Tyr Leu Ser Ala Lys Thr Phe Asp Asp Val Asp Lys Gly Ile Leu Gly
        610                 615                 620

Ala Thr Lys Trp Ile Lys Glu Asn Tyr Ile Asp Arg Gly Arg Thr Phe
625                 630                 635                 640

Leu Gly Asn Lys Ala Ser Gly Met Asn Val Glu Tyr Ala Ser Asp Pro
                645                 650                 655

Tyr Trp Gly Glu Lys Ile Ala Ser Val Met Met Lys Ile Asn Glu Lys
            660                 665                 670

Leu Gly Gly Lys Asp
            675
```

```
<210> SEQ ID NO 5
<211> LENGTH: 702
<212> TYPE: PRT
<213> ORGANISM: Streptococcus pneumoniae

<400> SEQUENCE: 5

Met Lys Lys Val Arg Phe Ile Phe Leu Ala Leu Leu Phe Phe Leu Ala
1               5                   10                  15

Ser Pro Glu Gly Ala Met Ala Ser Asp Gly Thr Trp Gln Gly Lys Gln
            20                  25                  30

Tyr Leu Lys Glu Asp Gly Ser Gln Ala Ala Asn Glu Trp Val Phe Asp
        35                  40                  45

Thr His Tyr Gln Ser Trp Phe Tyr Ile Lys Ala Asp Ala Asn Tyr Ala
    50                  55                  60

Glu Asn Glu Trp Leu Lys Gln Gly Asp Asp Tyr Phe Tyr Leu Lys Ser
65                  70                  75                  80

Gly Gly Tyr Met Ala Lys Ser Glu Trp Val Glu Asp Lys Gly Ala Phe
                85                  90                  95

Tyr Tyr Leu Asp Gln Asp Gly Lys Met Lys Arg Asn Ala Trp Val Gly
            100                 105                 110

Thr Ser Tyr Val Gly Ala Thr Gly Ala Lys Val Ile Glu Asp Trp Val
        115                 120                 125

Tyr Asp Ser Gln Tyr Asp Ala Trp Phe Tyr Ile Lys Ala Asp Gly Gln
    130                 135                 140

His Ala Glu Lys Glu Trp Leu Gln Ile Lys Gly Lys Asp Tyr Tyr Phe
145                 150                 155                 160

Lys Ser Gly Gly Tyr Leu Leu Thr Ser Gln Trp Ile Asn Gln Ala Tyr
                165                 170                 175

Val Asn Ala Ser Gly Ala Lys Val Gln Gln Gly Trp Leu Phe Asp Lys
            180                 185                 190

Gln Tyr Gln Ser Trp Phe Tyr Ile Lys Glu Asn Gly Asn Tyr Ala Asp
        195                 200                 205

Lys Glu Trp Ile Phe Glu Asn Gly His Tyr Tyr Leu Lys Ser Gly Gly
    210                 215                 220

Gly Tyr Met Ala Ala Asn Glu Trp Ile Trp Asp Lys Glu Ser Trp Phe
225                 230                 235                 240

Tyr Leu Lys Phe Asp Gly Lys Ile Ala Glu Lys Glu Trp Val Tyr Asp
                245                 250                 255

Ser His Ser Gln Ala Trp Tyr Tyr Phe Lys Ser Gly Gly Tyr Met Ala
            260                 265                 270

Ala Asn Glu Trp Ile Trp Asp Lys Glu Ser Trp Phe Tyr Leu Lys Phe
        275                 280                 285

Asp Gly Lys Met Ala Glu Lys Glu Trp Val Tyr Asp Ser His Ser Gln
    290                 295                 300

Ala Trp Tyr Tyr Phe Lys Ser Gly Gly Tyr Met Thr Ala Asn Glu Trp
305                 310                 315                 320

Ile Trp Asp Lys Glu Ser Trp Phe Tyr Leu Lys Ser Asp Gly Lys Ile
                325                 330                 335

Ala Glu Lys Glu Trp Val Tyr Asp Ser His Ser Gln Ala Trp Tyr Tyr
            340                 345                 350

Phe Lys Ser Gly Gly Tyr Met Thr Ala Asn Glu Trp Ile Trp Asp Lys
        355                 360                 365

Glu Ser Trp Phe Tyr Leu Lys Ser Asp Gly Lys Met Ala Glu Lys Glu
    370                 375                 380

Trp Val Tyr Asp Ser His Ser Gln Ala Trp Tyr Tyr Phe Lys Ser Gly
```

```
                385                 390                 395                 400
Gly Tyr Met Ala Lys Asn Glu Thr Val Asp Gly Tyr Gln Leu Gly Ser
                    405                 410                 415

Asp Gly Lys Trp Leu Gly Gly Lys Ala Thr Asn Lys Asn Ala Ala Tyr
                420                 425                 430

Tyr Gln Val Val Pro Val Thr Ala Asn Val Tyr Asp Ser Asp Gly Glu
                435                 440                 445

Lys Leu Ser Tyr Ile Ser Gln Gly Ser Val Val Trp Leu Asp Lys Asp
            450                 455                 460

Arg Lys Ser Asp Asp Lys Arg Leu Ala Ile Thr Ile Ser Gly Leu Ser
465                 470                 475                 480

Gly Tyr Met Lys Thr Glu Asp Leu Gln Ala Leu Asp Ala Ser Lys Asp
                    485                 490                 495

Phe Ile Pro Tyr Tyr Glu Ser Asp Gly His Arg Phe Tyr His Tyr Val
                500                 505                 510

Ala Gln Asn Ala Ser Ile Pro Val Ala Ser His Leu Ser Asp Met Glu
                515                 520                 525

Val Gly Lys Lys Tyr Tyr Ser Ala Asp Gly Leu His Phe Asp Gly Phe
            530                 535                 540

Lys Leu Glu Asn Pro Phe Leu Phe Lys Asp Leu Thr Glu Ala Thr Asn
545                 550                 555                 560

Tyr Ser Ala Glu Glu Leu Asp Lys Val Phe Ser Leu Leu Asn Ile Asn
                    565                 570                 575

Asn Ser Leu Leu Glu Asn Lys Gly Ala Thr Phe Lys Glu Ala Glu Glu
                580                 585                 590

His Tyr His Ile Asn Ala Leu Tyr Leu Leu Ala His Ser Ala Leu Glu
                595                 600                 605

Ser Asn Trp Gly Arg Ser Lys Ile Ala Lys Asp Lys Asn Asn Phe Phe
            610                 615                 620

Gly Ile Thr Ala Tyr Asp Thr Thr Pro Tyr Leu Ser Ala Lys Thr Phe
625                 630                 635                 640

Asp Asp Val Asp Lys Gly Ile Leu Gly Ala Thr Lys Trp Ile Lys Glu
                    645                 650                 655

Asn Tyr Ile Asp Arg Gly Arg Thr Phe Leu Gly Asn Lys Ala Ser Gly
                660                 665                 670

Met Asn Val Glu Tyr Ala Ser Asp Pro Tyr Trp Gly Glu Lys Ile Ala
                675                 680                 685

Ser Val Met Met Lys Ile Asn Glu Lys Leu Gly Gly Lys Asp
            690                 695                 700

<210> SEQ ID NO 6
<211> LENGTH: 708
<212> TYPE: PRT
<213> ORGANISM: Streptococcus pneumoniae

<400> SEQUENCE: 6

Met Lys Lys Thr Thr Ile Leu Ser Leu Thr Thr Ala Ala Val Ile Leu
1               5                   10                  15

Ala Ala Tyr Val Pro Asn Glu Pro Ile Leu Ala Ala Tyr Val Pro Asn
                20                  25                  30

Glu Pro Ile Leu Ala Asp Thr Pro Ser Ser Glu Val Ile Lys Glu Thr
            35                  40                  45

Lys Val Gly Ser Ile Ile Gln Gln Asn Asn Ile Lys Tyr Lys Val Leu
        50                  55                  60

Thr Val Glu Gly Asn Ile Gly Thr Val Gln Val Gly Asn Gly Val Thr
```

```
              65                  70                  75                  80
Pro Val Glu Phe Glu Ala Gly Gln Asp Gly Lys Pro Phe Thr Ile Pro
                    85                  90                  95
Thr Lys Ile Thr Val Gly Asp Lys Val Phe Thr Val Thr Glu Val Ala
                   100                 105                 110
Ser Gln Ala Phe Ser Tyr Tyr Pro Asp Glu Thr Gly Arg Ile Val Tyr
                   115                 120                 125
Tyr Pro Ser Ser Ile Thr Ile Pro Ser Ser Ile Lys Lys Ile Gln Lys
            130                 135                 140
Lys Gly Phe His Gly Ser Lys Ala Lys Thr Ile Ile Phe Asp Lys Gly
145                 150                 155                 160
Ser Gln Leu Glu Lys Ile Glu Asp Arg Ala Phe Asp Phe Ser Glu Leu
                    165                 170                 175
Glu Glu Ile Glu Leu Pro Ala Ser Leu Glu Tyr Ile Gly Thr Ser Ala
                    180                 185                 190
Phe Ser Phe Ser Gln Lys Leu Lys Lys Leu Thr Phe Ser Ser Ser Ser
                    195                 200                 205
Lys Leu Glu Leu Ile Ser His Glu Ala Phe Ala Asn Leu Ser Asn Leu
            210                 215                 220
Glu Lys Leu Thr Leu Pro Lys Ser Val Lys Thr Leu Gly Ser Asn Leu
225                 230                 235                 240
Phe Arg Leu Thr Thr Ser Leu Asn Met Leu Met Leu Arg Gly Met Ile
                    245                 250                 255
Val Ala Ser Val Asp Gly Val Ser Phe Gln Ser Lys Thr Gln Leu Ile
                    260                 265                 270
Tyr Tyr Pro Ser Gln Lys Asn Asp Glu Ser Tyr Lys Thr Pro Lys Glu
                    275                 280                 285
Thr Lys Glu Leu Ala Ser Tyr Ser Phe Asn Lys Asn Ser Tyr Leu Lys
            290                 295                 300
Lys Leu Glu Leu Asn Glu Gly Leu Gln Lys Ile Gly Thr Phe Ala Phe
305                 310                 315                 320
Ala Asp Ala Thr Lys Leu Glu Glu Ile Ser Leu Pro Asn Ser Leu Glu
                    325                 330                 335
Thr Ile Glu Arg Leu Ala Phe Tyr Gly Asn Leu Glu Leu Lys Glu Leu
                    340                 345                 350
Ile Leu Pro Asp Asn Val Lys Asn Phe Gly Lys His Val Met Asn Gly
                    355                 360                 365
Leu Pro Lys Phe Leu Thr Leu Ser Gly Asn Asn Ile Asn Ser Leu Pro
            370                 375                 380
Ser Phe Phe Leu Ser Gly Val Leu Asp Ser Leu Lys Glu Ile His Ile
385                 390                 395                 400
Lys Asn Lys Ser Thr Glu Phe Ser Val Lys Lys Asp Thr Phe Ala Ile
                    405                 410                 415
Pro Glu Thr Val Lys Phe Tyr Val Thr Ser His Ile Lys Asp Val
                    420                 425                 430
Leu Lys Ser Asn Leu Ser Thr Ser Asn Asp Ile Ile Val Glu Lys Val
            435                 440                 445
Asp Asn Ile Lys Gln Glu Thr Asp Val Ala Lys Pro Lys Lys Asn Ser
            450                 455                 460
Asn Gln Gly Val Val Gly Trp Val Asp Lys Gly Leu Trp Tyr Tyr
465                 470                 475                 480
Leu Asn Glu Ser Gly Ser Met Ala Thr Gly Trp Val Lys Asp Lys Gly
                    485                 490                 495
```

```
Leu Trp Tyr Tyr Leu Asn Glu Ser Gly Ser Met Ala Thr Gly Trp Val
            500                 505                 510
Lys Asp Lys Gly Leu Trp Tyr Tyr Leu Asn Glu Ser Gly Ser Met Ala
        515                 520                 525
Thr Gly Trp Val Lys Asp Lys Gly Leu Trp Tyr Tyr Leu Asn Glu Ser
    530                 535                 540
Gly Ser Met Ala Thr Gly Trp Val Lys Asp Lys Gly Leu Trp Tyr Tyr
545                 550                 555                 560
Leu Asn Glu Ser Gly Ser Met Ala Thr Gly Trp Val Lys Asp Lys Gly
                565                 570                 575
Leu Trp Tyr Tyr Leu Asn Glu Ser Gly Ser Met Ala Thr Gly Trp Val
            580                 585                 590
Lys Asp Lys Gly Leu Trp Tyr Tyr Leu Asn Glu Ser Gly Ser Met Ala
        595                 600                 605
Thr Gly Trp Val Lys Asp Lys Gly Leu Trp Tyr Tyr Leu Asn Glu Ser
    610                 615                 620
Gly Ser Met Ala Thr Gly Trp Val Lys Asp Lys Gly Leu Trp Tyr Tyr
625                 630                 635                 640
Leu Asn Glu Ser Gly Ser Met Ala Thr Gly Trp Val Lys Asp Lys Gly
                645                 650                 655
Leu Trp Tyr Tyr Leu Asn Glu Ser Gly Ser Met Ala Thr Gly Trp Val
            660                 665                 670
Lys Asp Lys Gly Leu Trp Tyr Tyr Leu Asn Glu Ser Gly Ser Met Ala
        675                 680                 685
Thr Gly Trp Phe Lys Val Ser Gly Lys Trp Tyr Tyr Tyr Asn Ser
    690                 695                 700
Gly Asp Phe Ile
705

<210> SEQ ID NO 7
<211> LENGTH: 445
<212> TYPE: PRT
<213> ORGANISM: Streptococcus pneumoniae

<400> SEQUENCE: 7

Met Ala Asp Thr Pro Ser Ser Glu Val Ile Lys Glu Thr Lys Val Gly
1               5                   10                  15
Ser Ile Ile Gln Gln Asn Ile Lys Tyr Lys Val Leu Thr Val Glu
            20                  25                  30
Gly Asn Ile Gly Thr Val Gln Val Gly Asn Gly Val Thr Pro Val Glu
        35                  40                  45
Phe Glu Ala Gly Gln Asp Gly Lys Pro Phe Thr Ile Pro Thr Lys Ile
    50                  55                  60
Thr Val Gly Asp Lys Val Phe Thr Val Thr Glu Val Ala Ser Gln Ala
65                  70                  75                  80
Phe Ser Tyr Tyr Pro Asp Glu Thr Gly Arg Ile Val Tyr Tyr Pro Ser
                85                  90                  95
Ser Ile Thr Ile Pro Ser Ser Ile Lys Lys Ile Gln Lys Lys Gly Phe
            100                 105                 110
His Gly Ser Lys Ala Lys Thr Ile Ile Phe Asp Lys Gly Ser Gln Leu
        115                 120                 125
Glu Lys Ile Glu Asp Arg Ala Phe Asp Phe Ser Glu Leu Glu Glu Ile
    130                 135                 140
Glu Leu Pro Ala Ser Leu Glu Tyr Ile Gly Thr Ser Ala Phe Ser Phe
145                 150                 155                 160
```

```
Ser Gln Lys Leu Lys Lys Leu Thr Phe Ser Ser Ser Lys Leu Glu
            165                 170                 175

Leu Ile Ser His Glu Ala Phe Ala Asn Leu Ser Asn Leu Glu Lys Leu
        180                 185                 190

Thr Leu Pro Lys Ser Val Lys Thr Leu Gly Ser Asn Leu Phe Arg Leu
            195                 200                 205

Thr Thr Ser Leu Lys His Val Asp Val Glu Glu Gly Asn Glu Ser Phe
        210                 215                 220

Ala Ser Val Asp Gly Val Leu Phe Ser Lys Asp Lys Thr Gln Leu Ile
225                 230                 235                 240

Tyr Tyr Pro Ser Gln Lys Asn Asp Glu Ser Tyr Lys Thr Pro Lys Glu
            245                 250                 255

Thr Lys Glu Leu Ala Ser Tyr Ser Phe Asn Lys Asn Ser Tyr Leu Lys
            260                 265                 270

Lys Leu Glu Leu Asn Glu Gly Leu Gly Lys Ile Gly Thr Phe Ala Phe
            275                 280                 285

Ala Asp Ala Ile Lys Leu Glu Glu Ile Ser Leu Pro Asn Ser Leu Glu
            290                 295                 300

Thr Ile Glu Arg Leu Ala Phe Tyr Gly Asn Leu Glu Leu Lys Glu Leu
305                 310                 315                 320

Ile Leu Pro Asp Asn Val Lys Asn Phe Gly Lys His Val Met Asn Gly
            325                 330                 335

Leu Pro Lys Leu Lys Ser Leu Thr Ile Gly Asn Asn Ile Asn Ser Leu
            340                 345                 350

Pro Ser Phe Phe Leu Ser Gly Val Leu Asp Ser Leu Lys Glu Ile His
            355                 360                 365

Ile Lys Asn Lys Ser Thr Glu Phe Ser Val Lys Asp Thr Phe Ala
            370                 375                 380

Ile Pro Glu Thr Val Lys Phe Tyr Val Thr Ser Glu His Ile Lys Asp
385                 390                 395                 400

Val Leu Lys Ser Asn Leu Ser Thr Ser Asn Asp Ile Ile Val Glu Lys
            405                 410                 415

Val Asp Asn Ile Lys Gln Glu Thr Asp Val Ala Lys Pro Lys Lys Asn
            420                 425                 430

Ser Asn Gln Gly Val Val Gly Trp Val Lys Asp Lys Gly
            435                 440                 445

<210> SEQ ID NO 8
<211> LENGTH: 280
<212> TYPE: PRT
<213> ORGANISM: Streptococcus pneumoniae

<400> SEQUENCE: 8

Gly Lys Ala Thr Asn Glu Asn Ala Ala Tyr Tyr Gln Val Val Pro Val
1               5                   10                  15

Thr Ala Asn Val Tyr Asp Ser Asp Gly Glu Lys Leu Ser Tyr Ile Ser
            20                  25                  30

Gln Gly Ser Val Val Trp Leu Asp Lys Asp Arg Lys Ser Asp Asp Lys
        35                  40                  45

Arg Leu Ala Ile Thr Ile Ser Gly Leu Ser Gly Tyr Met Lys Thr Glu
    50                  55                  60

Asp Leu Gln Ala Leu Asp Ala Ser Lys Asp Phe Ile Pro Tyr Tyr Glu
65                  70                  75                  80

Ser Asp Gly His Arg Phe Tyr His Tyr Val Ala Gln Asn Ala Ser Ile
            85                  90                  95
```

-continued

```
Pro Val Ala Ser His Leu Ser Asp Met Ala Val Gly Lys Lys Tyr Tyr
            100                 105                 110
Ser Ala Asp Gly Leu His Phe Asp Gly Phe Lys Leu Glu Asn Pro Phe
            115                 120                 125
Leu Phe Lys Asp Leu Thr Glu Ala Thr Asn Tyr Ser Ala Glu Glu Leu
        130                 135                 140
Asp Lys Val Phe Ser Leu Leu Asn Ile Asn Asn Ser Leu Leu Glu Asn
145                 150                 155                 160
Lys Gly Ala Thr Phe Lys Glu Ala Glu Glu His Tyr His Ile Asn Ala
                165                 170                 175
Leu Tyr Leu Leu Ala His Ser Ala Leu Glu Ser Asn Trp Gly Arg Ser
            180                 185                 190
Lys Ile Ala Lys Asp Lys Asn Asn Phe Phe Gly Ile Thr Ala Tyr Asp
            195                 200                 205
Thr Thr Pro Tyr Leu Ser Ala Lys Thr Phe Asp Asp Val Asp Lys Gly
        210                 215                 220
Ile Leu Gly Ala Thr Lys Trp Ile Lys Glu Asn Tyr Ile Asp Arg Gly
225                 230                 235                 240
Arg Thr Phe Leu Gly Asn Lys Ala Ser Gly Met Asn Val Glu Tyr Ala
                245                 250                 255
Ser Asp Pro Tyr Trp Gly Glu Lys Ile Ala Ser Val Met Met Lys Ile
            260                 265                 270
Asn Glu Lys Leu Gly Gly Lys Asp
            275                 280
```